United States Patent
Kaplan

(10) Patent No.: US 10,498,687 B2
(45) Date of Patent: Dec. 3, 2019

(54) PRIORITY BASED COMMUNICATION AND ORGANIZATION SYSTEM

(71) Applicant: Teleport Med, LLC, Miami, FL (US)

(72) Inventor: Lee D. Kaplan, Coconut Grove, FL (US)

(73) Assignee: TELEPORT MED, LLC, Miami, FL (US)

( * ) Notice: Subject to any disclaimer, the term of this patent is extended or adjusted under 35 U.S.C. 154(b) by 233 days.

(21) Appl. No.: 15/135,967

(22) Filed: Apr. 22, 2016

(65) Prior Publication Data

US 2016/0315898 A1 Oct. 27, 2016

Related U.S. Application Data

(60) Provisional application No. 62/151,525, filed on Apr. 23, 2015.

(51) Int. Cl.
*H04L 12/58* (2006.01)
*G06Q 10/10* (2012.01)
*G06Q 50/22* (2018.01)
*G16H 80/00* (2018.01)

(52) U.S. Cl.
CPC ............ *H04L 51/26* (2013.01); *G06Q 10/10* (2013.01); *G06Q 50/22* (2013.01); *G16H 80/00* (2018.01); *H04L 51/043* (2013.01); *H04L 51/046* (2013.01)

(58) Field of Classification Search
CPC ....... H04L 51/26; H04L 51/046; H04L 51/24; G06F 19/3425; G06Q 50/22; G06Q 10/10
See application file for complete search history.

(56) References Cited

U.S. PATENT DOCUMENTS

| 8,595,302 B2* | 11/2013 | Krishnamurthi ........ H04L 51/34 709/206 |
| 8,825,786 B1 | 9/2014 | Webb et al. |
| 2007/0022157 A1 | 1/2007 | Daniels et al. |
| 2009/0299934 A1* | 12/2009 | Horvitz ................ G05B 19/404 706/45 |
| 2010/0223071 A1* | 9/2010 | Kland .............. G06Q 10/06316 705/3 |
| 2011/0320221 A1 | 12/2011 | Duffey-Rosenstein et al. |
| 2012/0170721 A1 | 7/2012 | Yoakum |

(Continued)

OTHER PUBLICATIONS

Apptix, "Instant Messaing and Presence with Microsoft Lync;" Apr. 8, 2014, http://www.apptix.com/support/instant-messaging/lync-user-guides/lync-im-and-presence-guide.aspx.*

(Continued)

*Primary Examiner* — Ranodhi Serrao
(74) *Attorney, Agent, or Firm* — Foley & Lardner LLP

(57) ABSTRACT

A method includes receiving, by a receiver device, a request sent from a transmitter device. The request is identified by a case name and at least one of a type of the request and a due date of the request. The request has a transmitter priority designated by the transmitter device. The method also includes assigning, by the receiver device, a receiver priority for the request received by the receiver device. The method also includes determining a final priority by the receiver device. The final priority is based upon a combination of the transmitter priority and the receiver priority. The method further includes handling the request within the receiver device based on the final priority.

19 Claims, 27 Drawing Sheets

(56) References Cited

U.S. PATENT DOCUMENTS

| | | | | |
|---|---|---|---|---|
| 2013/0218553 A1* | 8/2013 | Fujii | ............ | G10L 15/26 704/9 |
| 2013/0325990 A1 | 12/2013 | Tysowski et al. | | |
| 2014/0101611 A1* | 4/2014 | Lang | ............ | G06F 21/32 715/813 |
| 2014/0282016 A1* | 9/2014 | Hosier, Jr. | ............ | H04W 4/08 715/733 |

OTHER PUBLICATIONS

Microsoft Office Labs, "Project: Email Prioritizer;" Aug. 22, 2008, http://www.officelabs.com/projects/emailprioritizer/Pages/default.aspx.*

Business Productivity, "5 steps to improve communication using microsoft lync;" Oct. 15, 2012, http://www.businessproductivity.com/5-steps-to-improve-communication-using-microsoft-lync/.*

Cox-Havron, Anna K., "Prioritizing Your Incoming Messages," Jul. 2005, https://www.aafp.org/fpm/2005/0700/p76.html (Year: 2005).*

"DocbookMD," accessed at https://www.docbookmd.com/features/, originally accessed on Feb. 16, 2015 (3 pages).

"OnPage Secure messaging & Pager Replacement," accessed at http://onpage.com/home/secure_messaging/secure-messaging-and-pager-features/, originally accessed on Feb. 16, 2015 (2 pages).

"PerfectServe," accessed at http://www.perfectserve.com/what-does-perfectserve-synchrony-do/, originally accessed on Feb. 16, 2015 (6 pages).

"Spok Mobile," accessed at http://cloud.spok.com/BR-AMER-Spok-Mobile-Healthcare.pdf, originally accessed on Feb. 16, 2015 (4 pages).

"Voalte Me," accessed at http://www.voalte.com/platform/collaboration/voalte-me/, originally accessed on Feb. 16, 2016 (2 pages).

"Voalte One," accessed at http://www.voalte.com/platform/collaboration/voalte-one/, originally accessed on Feb. 16, 2015 (2 pages).

* cited by examiner

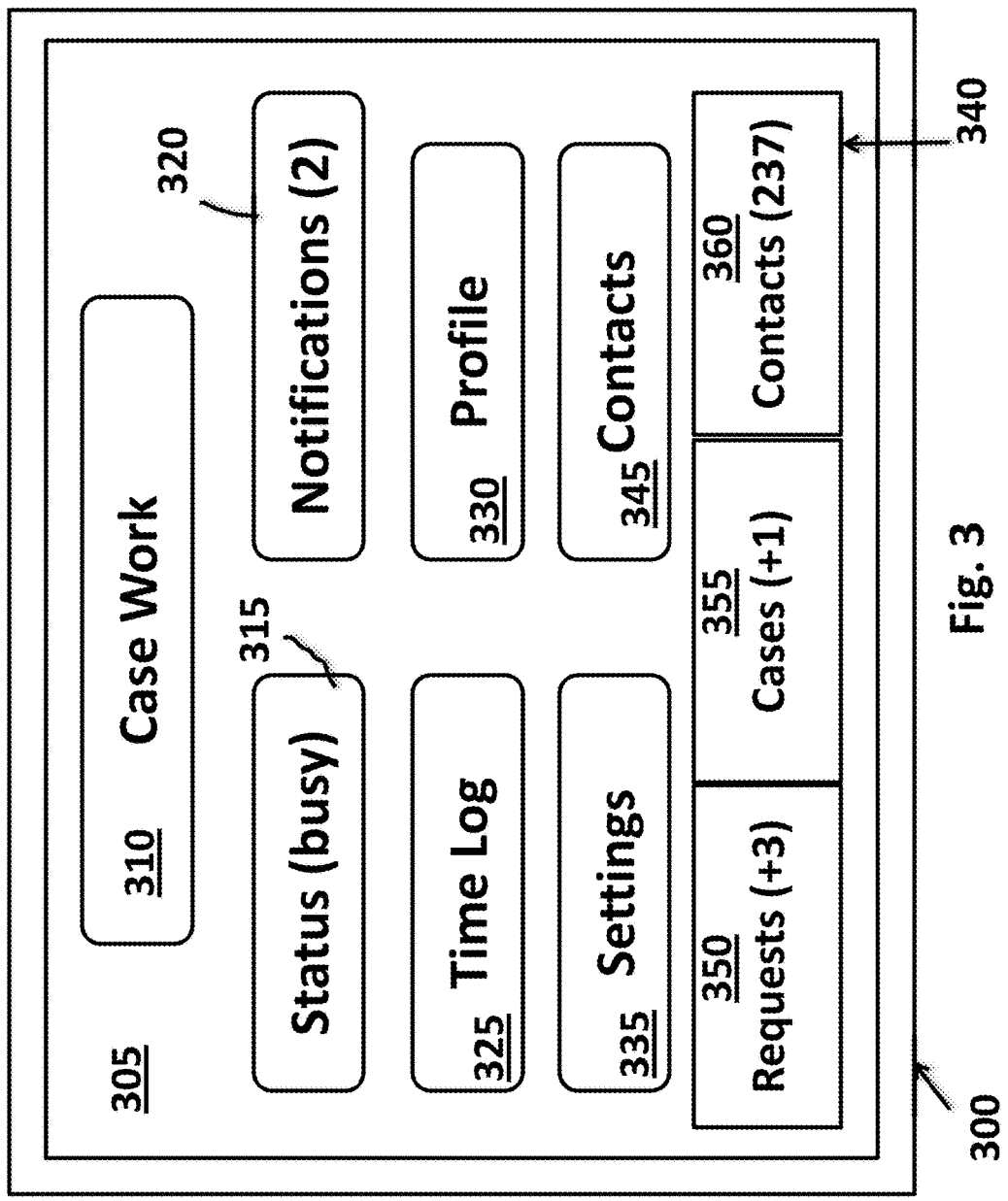

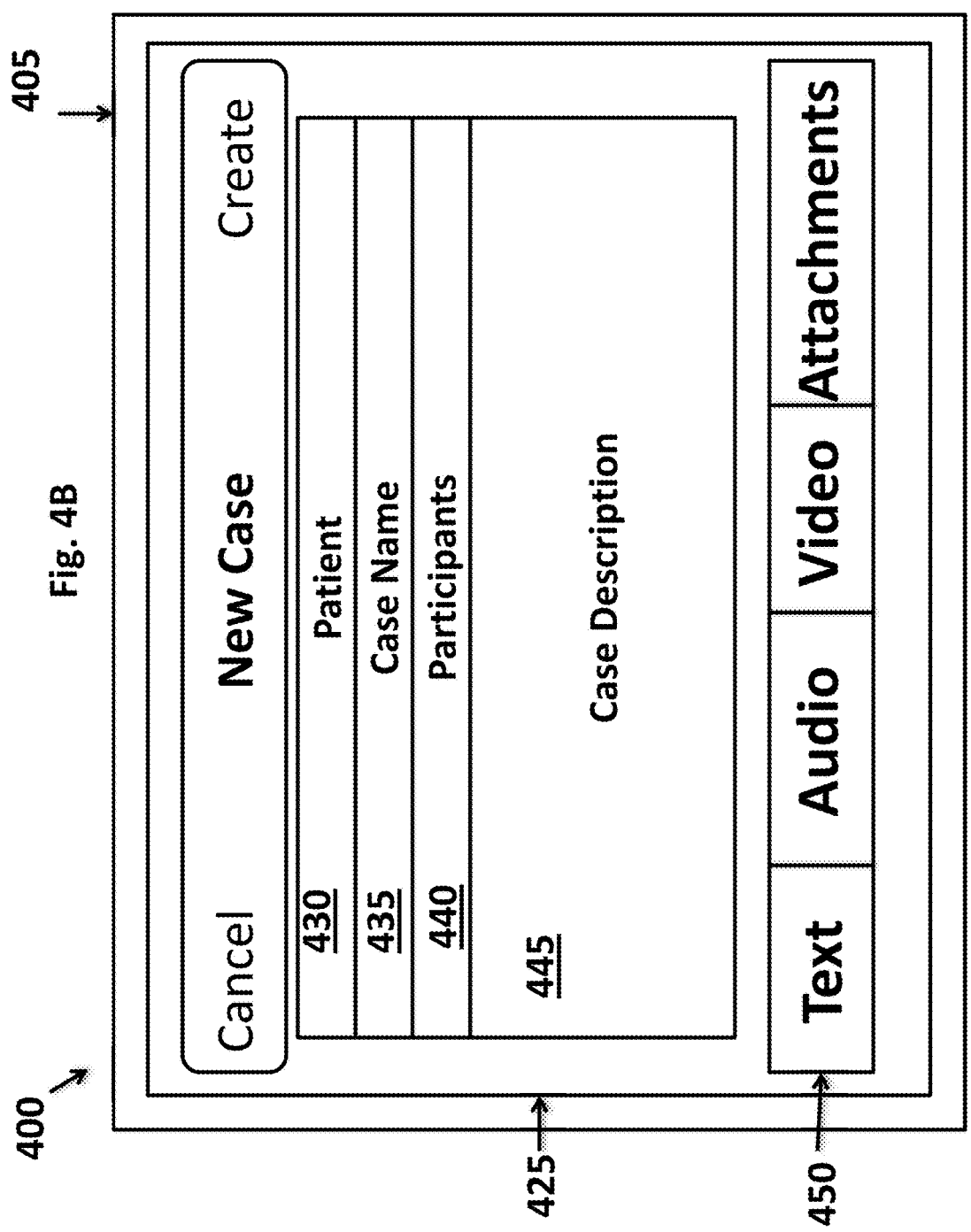

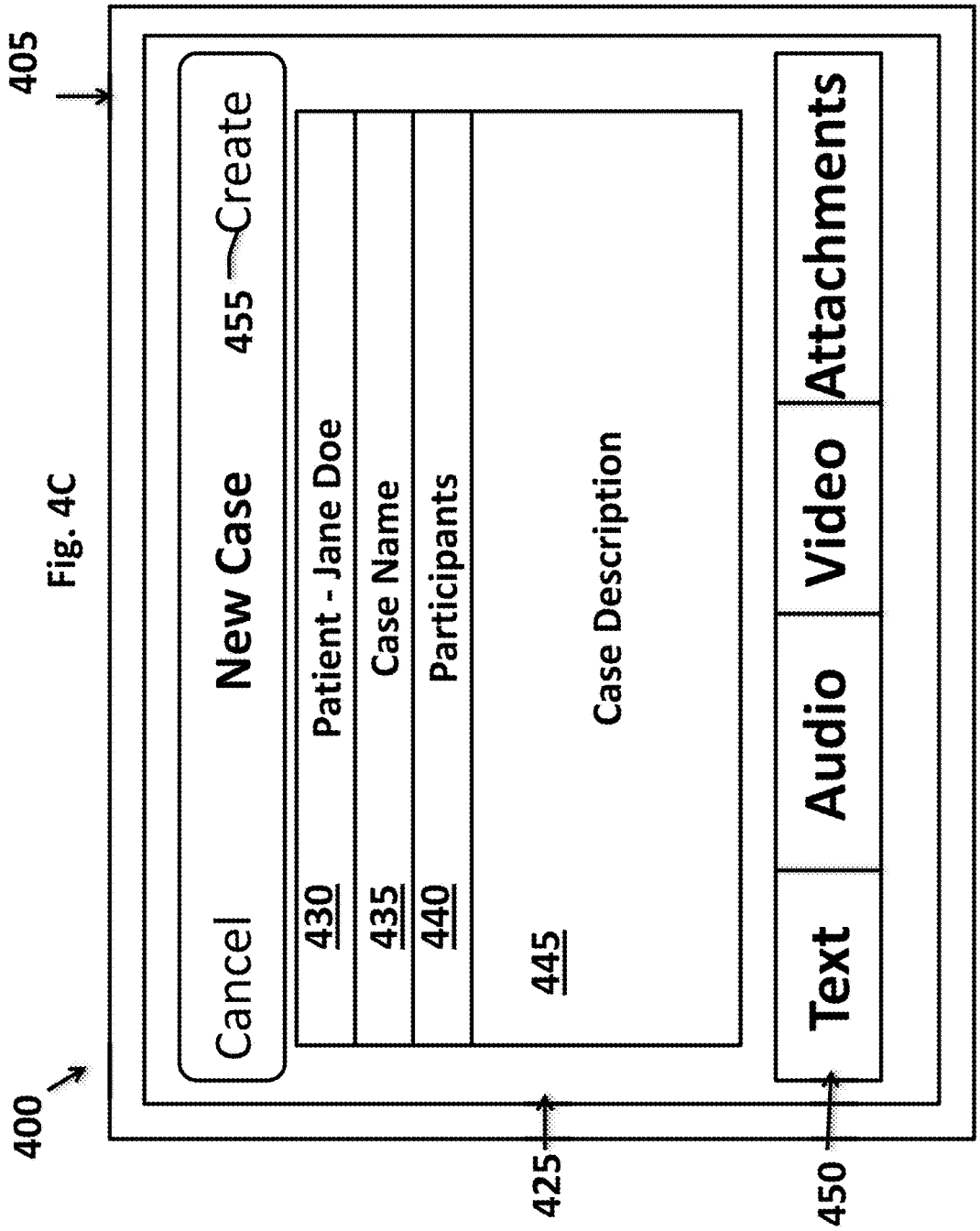

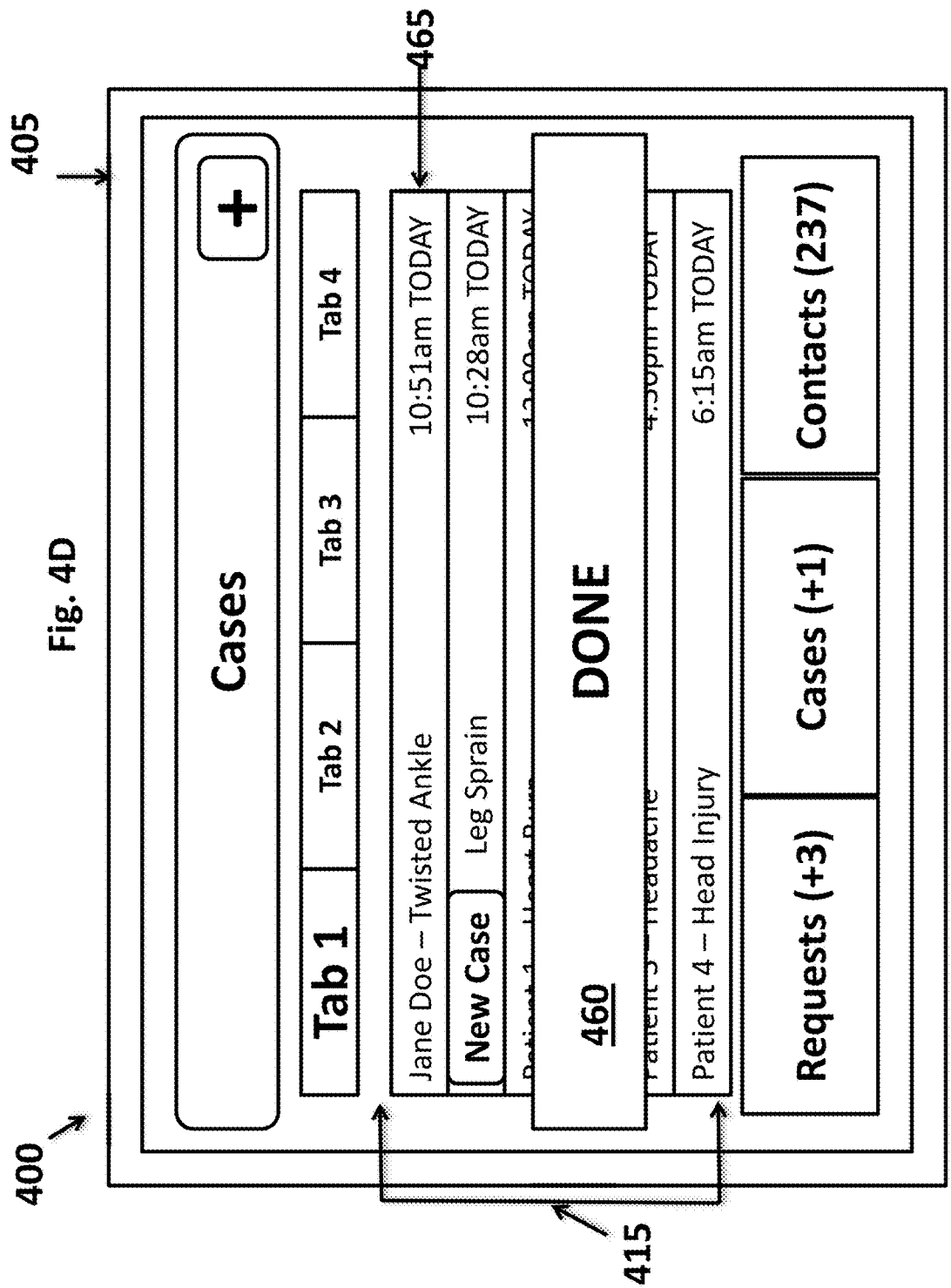

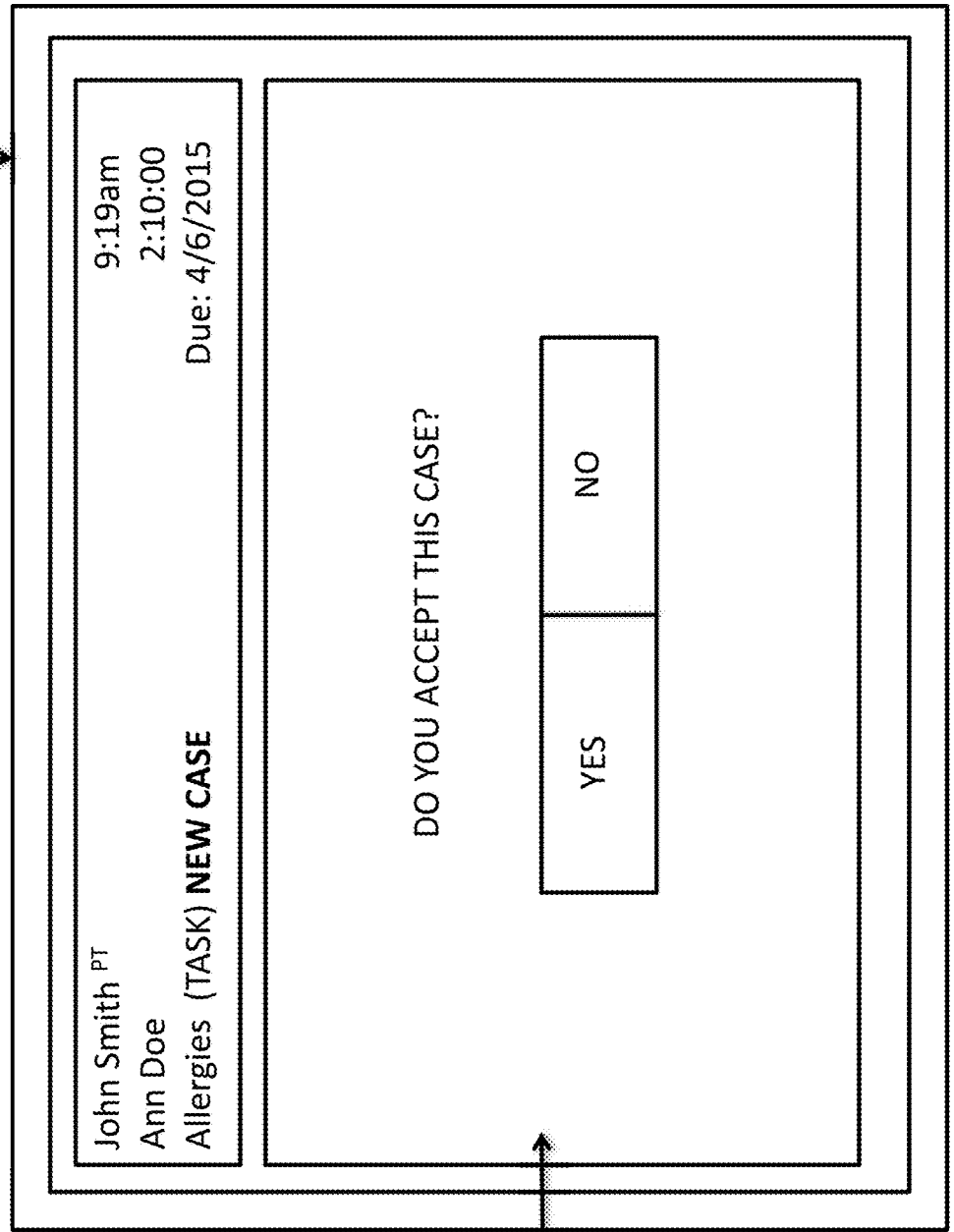

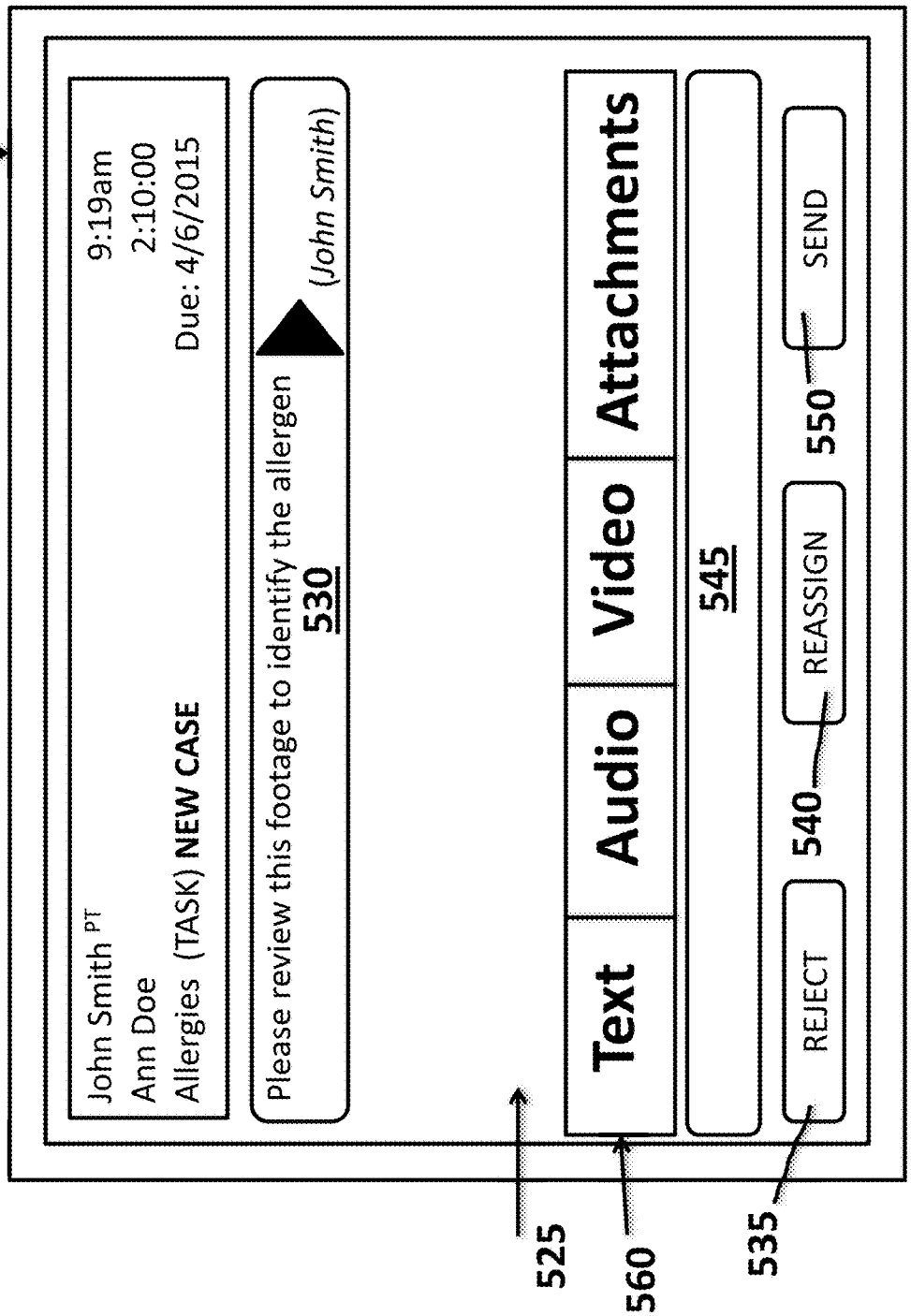

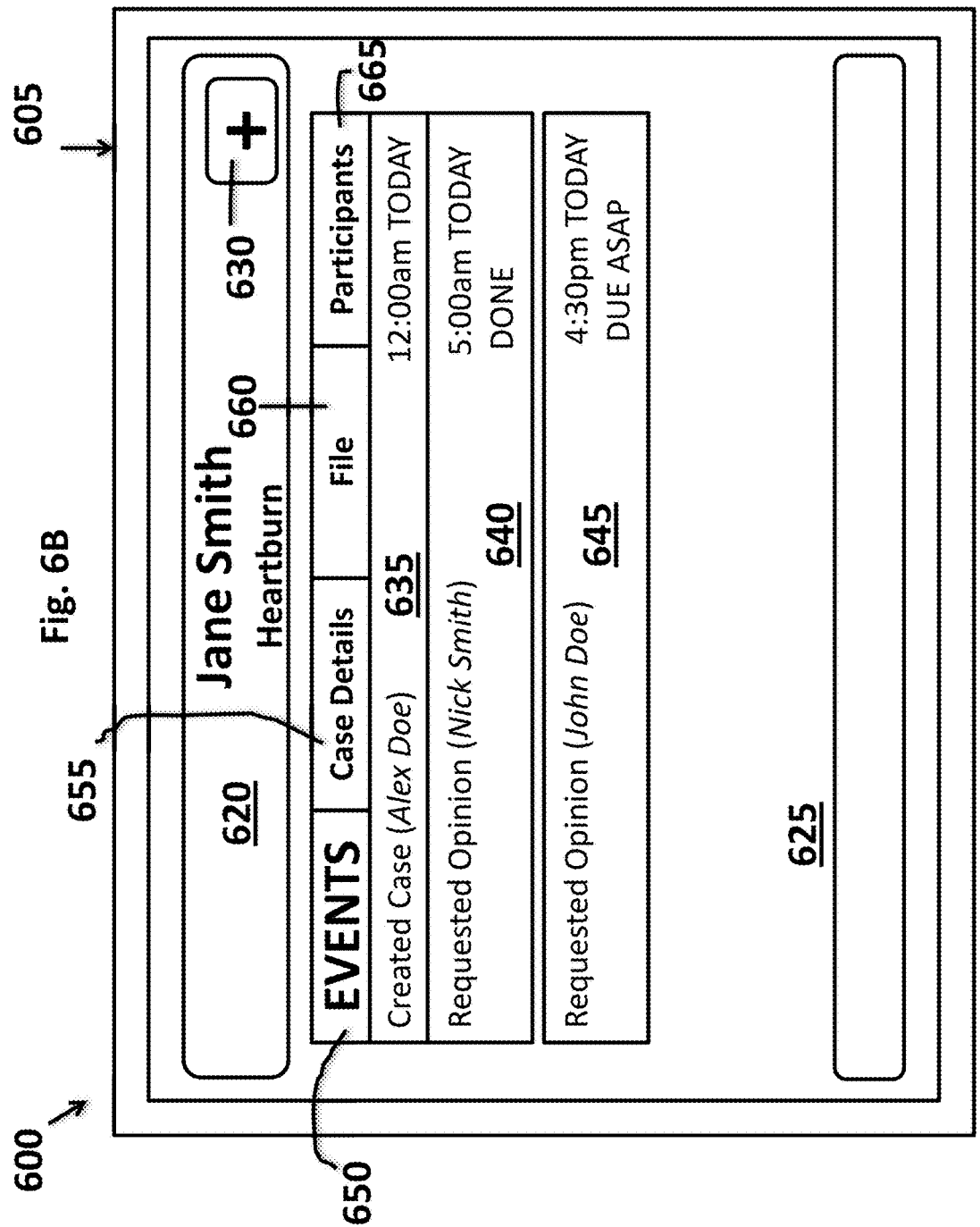

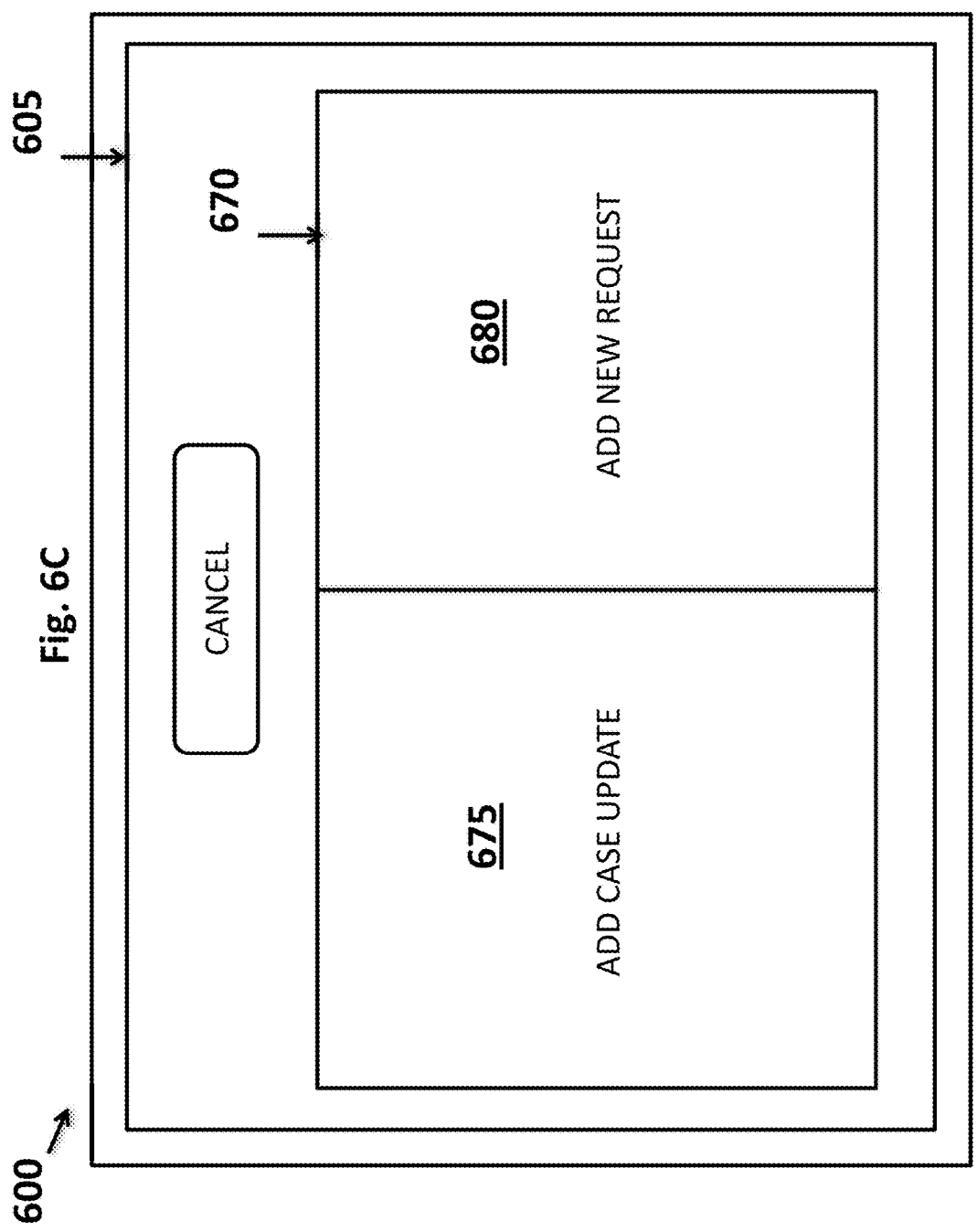

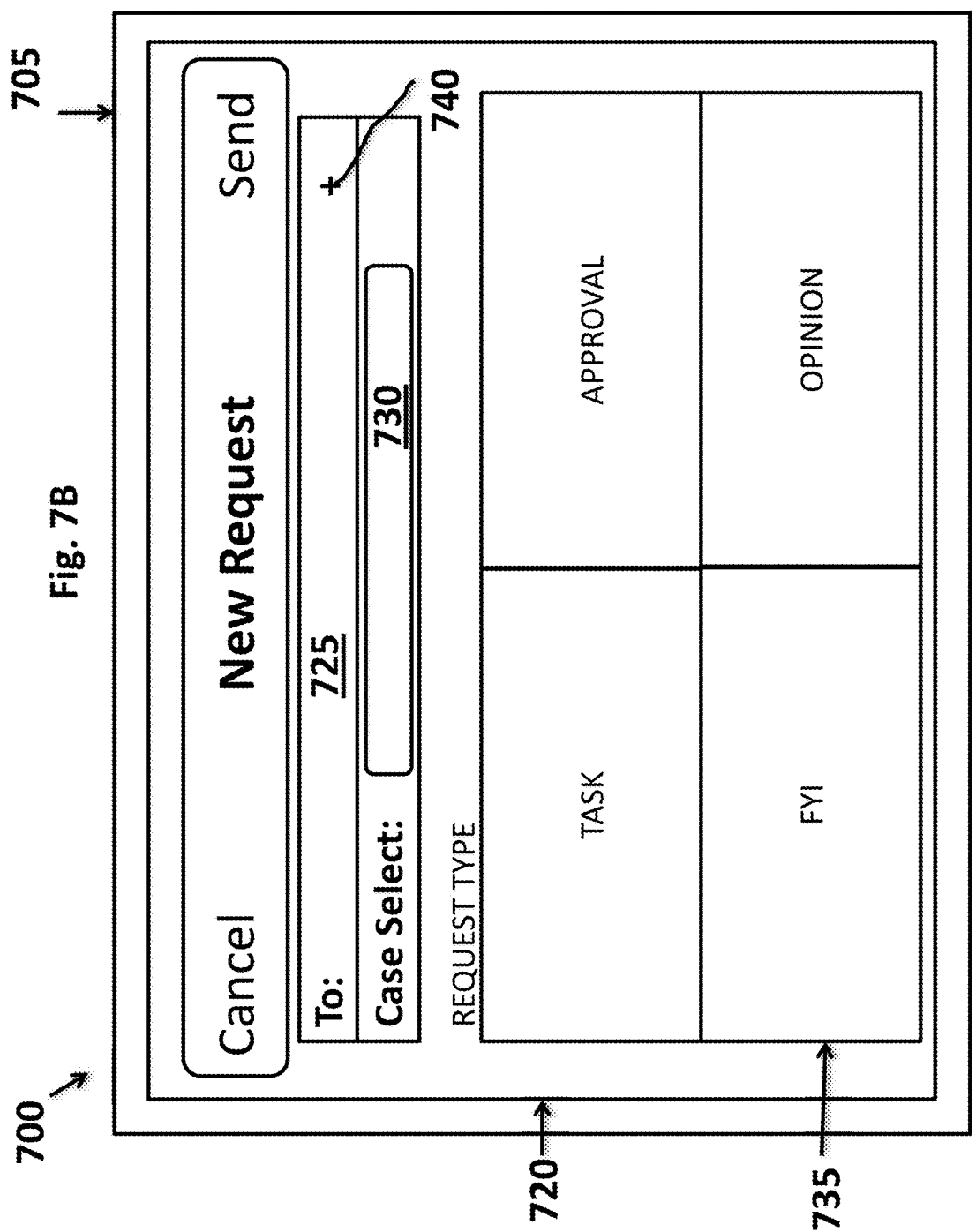

Fig. 7C

New Request

Cancel — Send

To: John Smith
Case Select: Jane Doe: Twisted Ankle
Request Type: TASK

URGENCY

| Normal | Urgent | Critical |

| No Due Date | Tomorrow | ASAP |

DUE

CUSTOM

NOTES:

Fig. 7D

New Request

Cancel — Send 770

To: John Smith

Case Select: Jane Doe: Twisted Ankle  +

Request Type: TASK

Urgency: NORMAL

Due: NO DUE DATE

NOTES:

760

Text | Audio | Video | Attachments

705 →

700 →

765 →

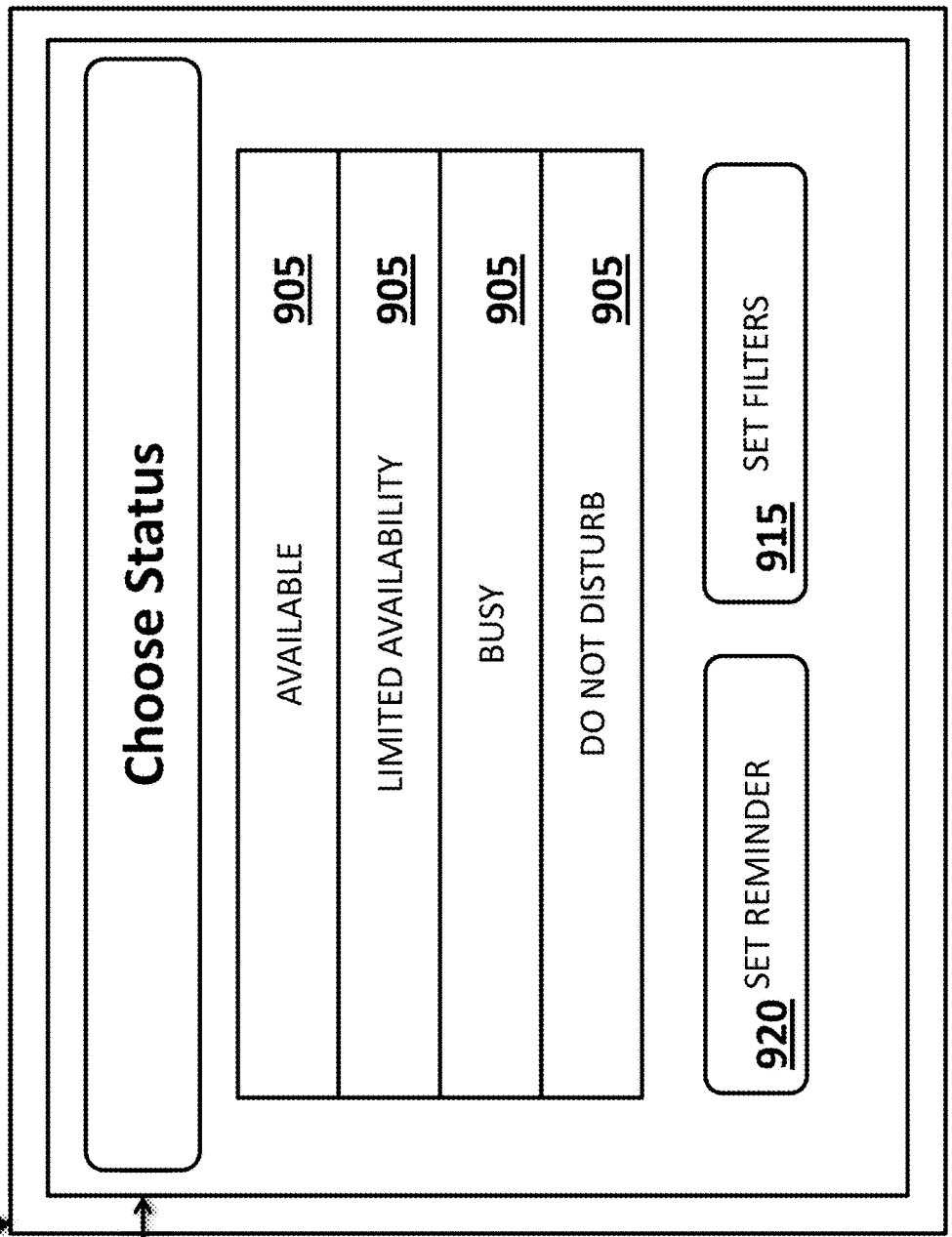

# PRIORITY BASED COMMUNICATION AND ORGANIZATION SYSTEM

CROSS-REFERENCE TO RELATED APPLICATIONS

The present application claims the benefit of U.S. Provisional Patent App. No. 62/151,525 filed on Apr. 23, 2015, the entire disclosure of which is hereby incorporated by reference herein.

BACKGROUND

Health care practitioners, in rendering care to their patients, often need to collaborate with other medical and non-medical caregivers. While these caregivers may be readily accessible to the health care practitioners for a face-to-face conversation, in at least some instances, the health care practitioners may need to remotely collaborate with the caregivers to share or gather information about their patients. Effective communication between the health care practitioners and the caregivers is key to providing timely and effective care to patients, while reducing health care costs.

SUMMARY

In accordance with at least some aspects of the present disclosure, a method is disclosed. The method includes receiving, by a receiver device, a request sent from a transmitter device. The request is identified by a case name and at least one of a type of the request and a due date of the request. The request has a transmitter priority designated by the transmitter device. The method also includes assigning, by the receiver device, a receiver priority for the request received by the receiver device. The method also includes determining a final priority by the receiver device. The final priority is based upon a combination of the transmitter priority and the receiver priority. The method further includes handling the request within the receiver device based on the final priority.

In accordance with at least some other aspects of the present disclosure, a receiver device is disclosed. The receiver device includes a memory configured to store application software, a controller, and a receiver. The receiver is configured to receive a request from a transmitter device, wherein the request is identified by a case name and at least one of a type of the request and a due date of the request, and wherein the request has a transmitter priority designated by the transmitter device. The controller is configured to assign the request a receiver priority, determine a final priority based upon the transmitter priority and the receiver priority, and manage notification of the request based upon the final priority.

In accordance with other aspects of the present disclosure, a non-transitory computer-readable medium is disclosed. The computer-readable medium has instructions stored thereon that, upon execution by a computing device, cause the computing device to perform operations. The instructions include instructions to receive a request from a transmitter device, wherein the request is identified by a case name and at least one of a type of the request and a due date of the request, and wherein the request has a transmitter priority designated by the transmitter device. The instructions also include instructions to assign a receiver priority to the request, instructions to determine a final priority based at least in part on the transmitter priority and the receiver priority, and instructions to manage notification of the request based upon the final priority.

The foregoing is a summary of the disclosure and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined by the claims, will become apparent in the detailed description set forth herein and taken in conjunction with the accompanying drawings.

BRIEF DESCRIPTION OF THE DRAWINGS

FIG. 3 is an illustrative screenshot of an overall panel showing at least some features of an application software installed on the first device and the second device of FIG. 2, in accordance with at least some embodiments of the present disclosure.

FIGS. 4A-4D are illustrative block diagrams showing a case creation feature of the application software of FIG. 3, in accordance with at least some embodiments of the present disclosure.

FIGS. 5A-5D are illustrative block diagrams showing a request responding feature of the application software of FIG. 3, in accordance with at least some embodiments of the present disclosure.

FIGS. 6A-6D are illustrative block diagrams showing a case management feature of the application software of FIG. 3, in accordance with at least some embodiments of the present disclosure.

FIGS. 7A-7D are illustrative block diagrams showing yet another case management feature of the application software of FIG. 3, in accordance with at least some embodiments of the present disclosure.

FIG. 9 is an illustrative block diagram showing various ways of prioritizing the communications of FIG. 8, in accordance with at least some embodiments of the present disclosure.

FIG. 13 depicts a case list of a caregiver associated with the case from FIG. 12, in accordance with an illustrative embodiment.

DETAILED DESCRIPTION

The present disclosure relates to an application software for facilitating communications between health care practitioners and caregivers for rendering care to one or more patients. By virtue of using the application software, communications in a medical team (e.g., including health care practitioners and caregivers) may be streamlined and enhanced by affording the members of the team an effective way to communicate and collaborate with one another. Specifically, features of the application software may allow for case creation and access, such that all communications pertaining to a particular patient may be organized in its own separate case, communications may be prioritized, deliberately documented with a date and time stamp to create a medical record, and all communications may have the ability to send varying types of information, such as text, audio, video, photographs, etc. Additionally, participants may be easily added to a case, a web or mobile application may be used for accessing the application software anywhere and anytime, and location of a case may be documented to take advantage of local resources. All of the above features provide for an appealing and efficient user experience for the medical team engaged in medical collaboration.

Figure 1:
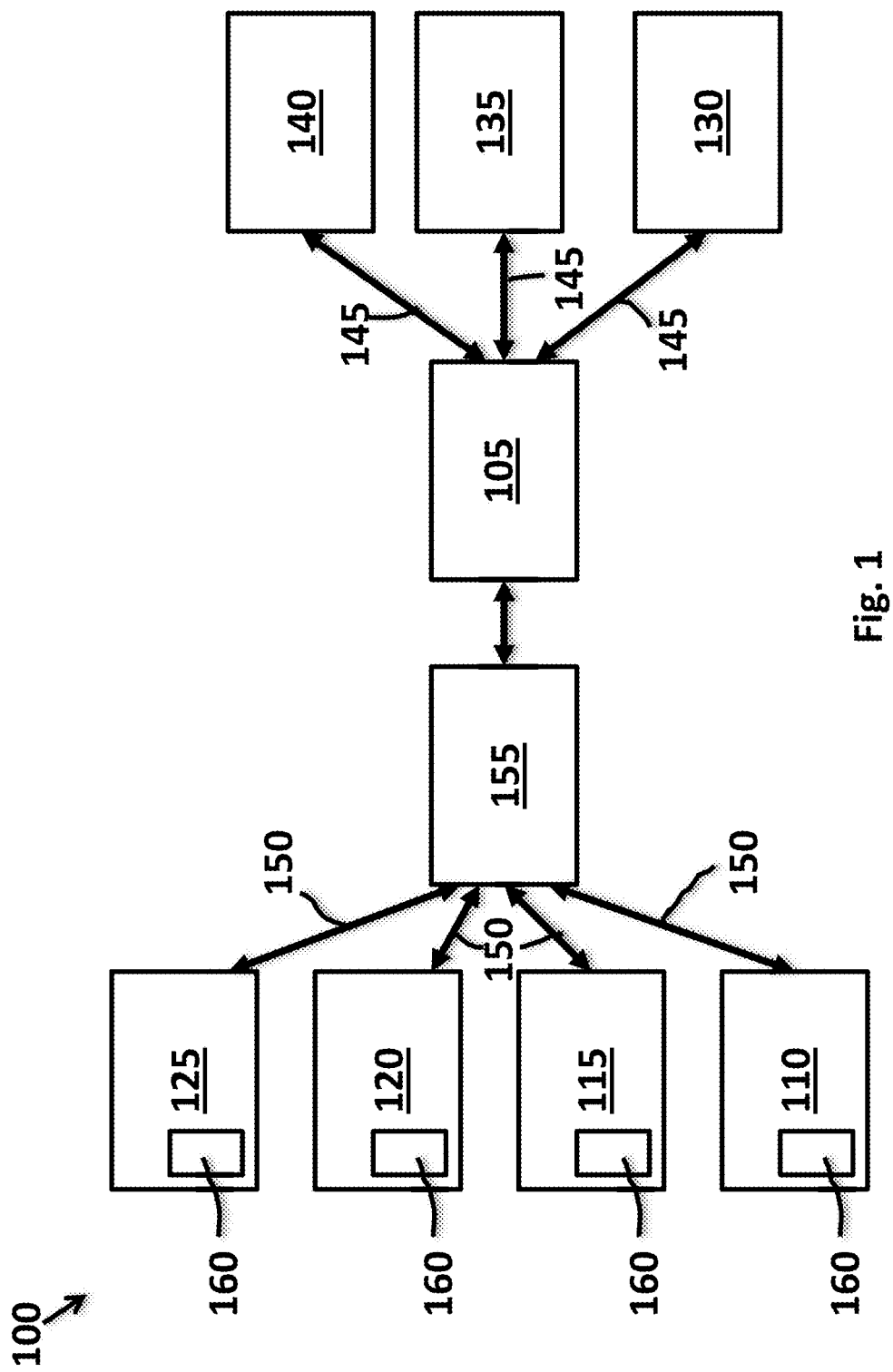
FIG. 1 is an illustrative diagram of a communication system, in accordance with at least some embodiments of the present disclosure.

Referring now to FIG. 1, a communication system 100, is shown in accordance with at least some embodiments of the present disclosure. As shown, the communication system 100 may include a health care practitioner 105 in at least indirect communication with caregivers 110, 115, 120, and 125 for facilitating care of patients 130, 135, and 140. In at least some embodiments, the health care practitioner 105 may also be in at least indirect communication with the patients 130-140. The communication of the health care practitioner 105 with the patients 130-140 may be represented by communication links 145, while the communication of the health care practitioner with the caregivers 110-125 may be represented by communication links 150. Although not shown, as needed, the caregivers 110-125 may also be in at least indirect communication with one or more of the patients 130-140 and with one another in order to render care to those patients.

Furthermore, in at least some embodiments, the caregivers 110-125 may be doctors, nurses, physical therapists, occupational therapists, chiropractors, athletic trainers, nannies, or any other type of personnel involved in providing medical, non-medical, or therapeutic care and maintenance to one or more of the patients 130-140, or otherwise having information that may be useful in rendering care to those patients. Similarly, in at least some embodiments, the health care practitioner 105 may be a primary care provider of the patients 130-140. In other embodiments, the health care practitioner 105 may be a medical consultant or expert whose opinion may be necessary or desirable in rendering care to the patients 130-140 regardless of whether the health care practitioner may be personally involved in the care of those patients. The patients 130-140 may be any type of patients, including both human patients and animal patients.

Notwithstanding the fact that in the present embodiment, one health care practitioner (e.g., the health care practitioner 105) is shown as communicating with four caregivers (e.g., the caregivers 110-125) to facilitate care of three patients (e.g., the patients 130-140), the number of the health care practitioners, the caregivers, and the patients is merely illustrative. In other embodiments, the health care practitioner 105 may communicate with more or less than four of the caregivers 110-125 to facilitate care of more or less than three of the patients 130-140. Relatedly, more than one of the health care practitioner 105 may be involved in communicating with the caregivers 110-125 and the patients 130-140. Furthermore, in at least some embodiments, the number of the caregivers 110-125 that the health care practitioner 105 may communicate with for facilitating care of each of the patients 130-140 may vary. For example, in some embodiments, the health care practitioner 105 may communicate with multiple ones of the caregivers 110-125 to facilitate care of one of the patients 130-140, while in other embodiments, the health care practitioner may communicate with one caregiver to facilitate care of one or multiple number of patients.

Furthermore, in at least some embodiments, the health care practitioner 105 and the caregivers 110-125 may communicate with one another using a first device 155 and a second device 160. Thus, for example, communication between the health care practitioner 105 and the caregivers 110-125 may be facilitated via the first device 155 used by the health care practitioner and the second device 160 used by the caregivers. Furthermore, any communication amongst the caregivers 110-125 may also be facilitated using the second device 160 that each of the caregivers operates. Additionally, while the patients 130-140 have not been shown herein as having either the first device 155 of the second device 160, in at least some embodiments, one or more of those patients may be given the first device or the second device to facilitate communications with the health care practitioner 105 and the caregivers 110-125.

Moreover, it is to be understood that the first device 155 and the second device 160 are named such merely for ease of explanation. Rather, depending upon whether those devices are receiving communications or transmitting communications, those devices may be appropriately thought of as either a "receiver device" or a "transmitter device." Specifically, a device may be deemed a "receiver device" if that device is configured to receive communications from other devices. Relatedly, a device may be deemed a "transmitter device" if that device is configured to transmit communications to other devices. In at least some embodiments, each of the first device 155 and the second device 160 may be configured to be both a "receiver device" and a "transmitter device" and may, therefore, be capable of both receiving and sending communications. The first device 155 and the second device 160 are described in greater detail below in FIG. 2.

Furthermore, in at least some embodiments, the communications between the health care practitioner 105 and the caregivers 110-125, and communications amongst the caregivers, may be organized into "cases." As used herein, "case," "cases," or another like term can refer to a medical record or a record of all communications pertaining to care of one patient, regardless of the party initiating or receiving the communication. Thus, each of the patients 130-140 may be represented by their individual case within the first device 155 and the second device 160. Creation and management of cases is described in greater detail below with respect to FIGS. 3-10B.

Figure 2:
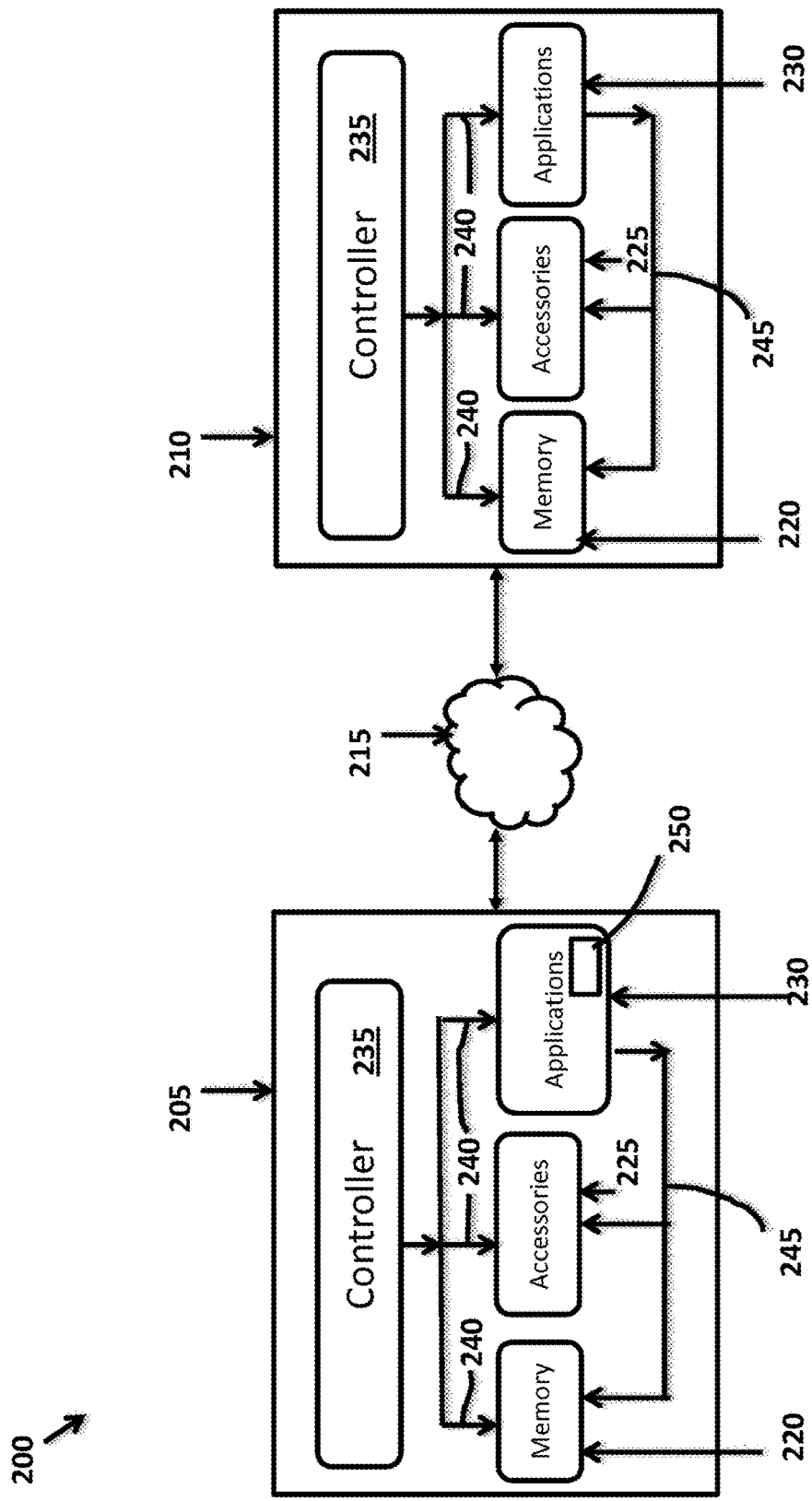
FIG. 2 is a simplified block diagram showing communication between a first device and a second device of the communication system of FIG. 1, in accordance with at least some embodiments of the present disclosure.

Turning now to FIG. 2, an illustrative block diagram 200 showing communication between a first device 205 and a second device 210 via a communication interface 215 is shown, in accordance with at least some embodiments of the present disclosure. The first device 205 corresponds to the first device 155, while the second device 210 corresponds to the second device 160, of FIG. 1. In at least some embodiments, each of the first device 205 and the second device 210 may be an electronic smart computing device. For example, in at least some embodiments, one or both of the first device 205 and the second device 210 may be a smart mobile phone, a tablet, a phablet, a personal digital assistant (PDA), an enterprise digital system (EDA), a smart watch, or other type of electronic handheld or wearable device that may be configured to facilitate communications, described in this disclosure, via the communication interface 215. In other embodiments, one or both of the first device 205 and the second device 210 may be a laptop, a desktop, or other electronic device that is not necessarily handheld but that may still be configured to facilitate communications described in this disclosure.

Additionally, each of the first device 205 and the second device 210 may include a memory 220, accessories 225, and applications 230. The memory 220, the accessories 225, and the applications 230, may all operate under control of a controller 235 (or processor), as shown by communication links 240. Notwithstanding the fact that, in the present embodiment, the first device 205 and the second device 210, are shown and described to have only the memory 220, the accessories 225, the applications 230, and the controller 235, several other components, subsystems, and devices, such as, sensors, power management subsystems, display subsystems, logic subsystems, amplifiers, interfaces, etc., that are commonly used in conjunction with the type of device embodying the first device and the second device, are contemplated and considered within the scope of the present disclosure. Also, the first device 205 and the second device 210 need not always have the same number and type of components. Rather, the number and type of components that each of the first device 205 and the second device 210 have may vary depending upon the type of device embodying the first device and the second device.

Thus, each of the first device 205 and the second device 210 may have several components including but not limited to, the memory 220, the accessories 225, the applications 230, and the controller 235. With respect to the memory 220 in particular, in at least some embodiments, it may include a variety of volatile and non-volatile memory/electronic storage, such as, random access memory (RAM), read only memory (ROM), dynamic random access memory (DRAM), programmable read only memory (PROM), erasable programmable read only memory (EPROM), electrically erasable programmable read only memory (EEPROM), flash memory, and the like. The memory 220, in addition to or instead of the above described memory/electronic storage, may also include storage in the form of compact disc (CD), digital video disc (DVD), floppy discs, Blu-ray discs, alternate optical storage, magnetic storage, cloud storage, computer readable media, or other type of electronic storage capability built into or attachable to the first device 205 and the second device 210.

With respect to the accessories 225, in at least some embodiments, they may include a keyboard, a screen, an audio subsystem, a video subsystem, camera, head-phone jack, general positioning system, microphone, and other types of input output systems that are commonly employed in, or configured to be coupled to, the type of device embodying the first device 205 and the second device 210. Relatedly, the applications 230 within each of the first device 205 and the second device 210 may be any of a variety of stand-alone application software (commonly known as "apps") configured to provide specialized functionalities within the first and the second devices. In at least some embodiments, at least some of the applications 230 may be pre-installed on the first device 205 and the second device 210 at the time of manufacture. In other embodiments, at least some of the applications 230 may be downloaded onto the first device 205 and the second device 210 by a user of that device as a web application from an application distribution platform, such as, the Apple App Store, Google Play, Windows App Store, and the like. Generally speaking, the applications 230 on each of the first device 205 and the second device 210 are likely to be a combination of pre-installed applications and downloadable applications. Furthermore, the applications 230 may utilize the memory 220 and one or more of the accessories 225, as shown by communication links 245, in order to operate under the control of the controller 235. Although not shown, the applications 230 may also utilize and interact with other hardware and software components on the first device 205 and the second device 210, such as, audio, video, camera, to be able to operate and function as intended.

One such application that may be installed (either pre-installed or downloaded) on the first device 205 and the second device 210 may be a medical application 250 for facilitating communications between the health care practitioner 105 and the caregivers 110-125 to render care to the patients 130-140, as described in FIG. 1. The medical application 250 may provide a variety of features including some core features, such as case creation and management, communication prioritization, universal access, date/time stamped communications, geo-position determination, participant management, etc. At least some of these features of the medical application 250 are described in greater detail with respect to FIGS. 3-10B below. Furthermore, the medical application 250 may be configured as a secure application, designed to comply with any regulatory or safety state or federal standards. For example, the medical application 250 may be configured to comply with the Health Insurance Portability and Accountability Act (HIPAA). The medical application 250 may also be configured to comply with other protocols and standards that govern medical communication between medical practitioners.

Referring still to FIG. 2, the controller 235 may include a digital signal processor (DSP), such as, a general-purpose stand alone or embedded processor, or a specialized processing unit suitable for the type of device embodying the first device 205 and the second device 210. In at least some embodiments, multiple processing units, connected together at least indirectly and utilized in combination with one another to perform various functions of the controller 235, may be used. The controller 235 may be equipped with a variety of components, subsystems, and devices configured to control and operate the memory 220, the accessories 225, the applications 230, as well as other hardware and software components of the first device 205 and the second device 210.

Furthermore, the controller 235 may be configured to process a variety of program instructions and data, in accordance with the present disclosure. These program instructions and data need not always be digital or composed in any high-level programming language. Rather, the program instructions may be any set of signal-producing or signal-altering circuitry or media that may be capable of performing functions, described in the present disclosure. Furthermore, the controller 235 may be located within the first device 205 and the second device 210, or alternatively, the controller may be located at a remote location or a cloud for communicating with the first device and the second device.

Thus, the first device 205 and the second device 210 may utilize all of the components described above (e.g., the memory 220, the accessories 225, the applications 230, and the controller 235) to facilitate communication with each other. As noted above, the communication between the first device 205 and the second device 210 may occur via the communication interface 215. In at least some embodiments, the communication interface 215 may be the World Wide Web (WWW), commonly known as the Internet. In other embodiments, the communication interface 215 may be the Ethernet, FireWire, Universal Serial Bus (USB), Near Field Communication (NFC), WiFi, WiMAX, 3G, 4G, 4G long-term evolution (LTE), Bluetooth, parallel ports, and other types of wired, wireless, radio, optical or, other types of interfaces and connections that may be suitable for communicating between the first device 205 and the second device 210. In yet other embodiments, the communication interface 215 may involve wireless chipsets, antennae, wired ports, signal converters, communication protocols like public switched telephone networks (PSTN), public switched data networks (PSDN), short messaging service (SMS) networks, local-area networks (LAN), voice over IP (VoIP) networks, wide area networks (WAN), virtual private networks (VPN), campus area networks, and other types of networks for facilitating communication. In at least some embodiments, the first device 205 and the second device 210 may be configured to communicate with one another via one or a combination of the communication interface 215, described above.

Turning now to FIGS. 3-10B, illustrative block diagrams and a flowchart describing various features of the medical application 250 of FIG. 2 to facilitate the communication described in FIG. 1 are shown, in accordance with at least some embodiments of the present disclosure. It is to be understood that only those features of the medical application 250 that are necessary for a proper understanding of the medical application are shown and described herein. Nevertheless, other features of the medical application (such as capturing photos and videos, connecting to calendars, etc.) that may be necessary or desirable for a proper functioning of the medical application 250 are contemplated and considered within a scope of the present disclosure.

Referring specifically to FIG. 3 now, an exemplary device 300 displaying an overall panel 305 of the medical application 250 of FIG. 2 is shown, in accordance with at least some embodiments of the present disclosure. The device 300 may correspond to either the first device 205 or the second device 210 described in FIG. 2 above and may, therefore, be either a receiver device or a transmitter device. Furthermore, in at least some embodiments, the device 300 may have the medical application 250 installed thereon, while in other embodiments, the device may be configured to access the medical application via a web application. The device 300 may be any one of the devices described above in FIG. 2 and have a shape and form corresponding to that device. Furthermore, the look, feel, layout and placement of the various buttons and other indicia on the device 300 may vary from one embodiment to another.

In at least some embodiments, the overall panel 305 may be one of the first screens that a user of the medical application 250 may view upon launching the medical application. The medical application 250 may be launched, in at least some embodiments, by clicking an icon of the medical application on the device 300 when the medical application is installed as an application software on the device. If the medical application 250 is accessed as a web application, then the medical application may be launched from a uniform resource identifier (such as a web link). In at least some embodiments, the medical application 250 may be password protected to prevent unauthorized access. Password protection may be achieved in any of a variety of commonly used ways, such as, by using patterns, finger print scanning, entering combinations of letters and numbers, etc. Furthermore, a "user" of the medical application 250 may either be the health care practitioner 105, the caregivers 110-125, or the patients 130-140 (although the patients may only have access to a limited number of features).

The overall panel 305 of the device 300, in at least some embodiments, may include a plurality of mini panels, each mini panel representing a different functionality. For example, in at least some embodiments, the overall panel 305 may have a case work mini panel 310, a status mini panel 315, a notifications mini panel 320, a time log mini panel 325, a profile mini panel 330, a settings mini panel 335, a summary mini panel 340, and a contacts mini panel 345. Notwithstanding the mini panels 310-345 described above, the number and the functionalities of those mini panels may vary based upon the features that may be desired in the medical application 250.

Figure 4A:
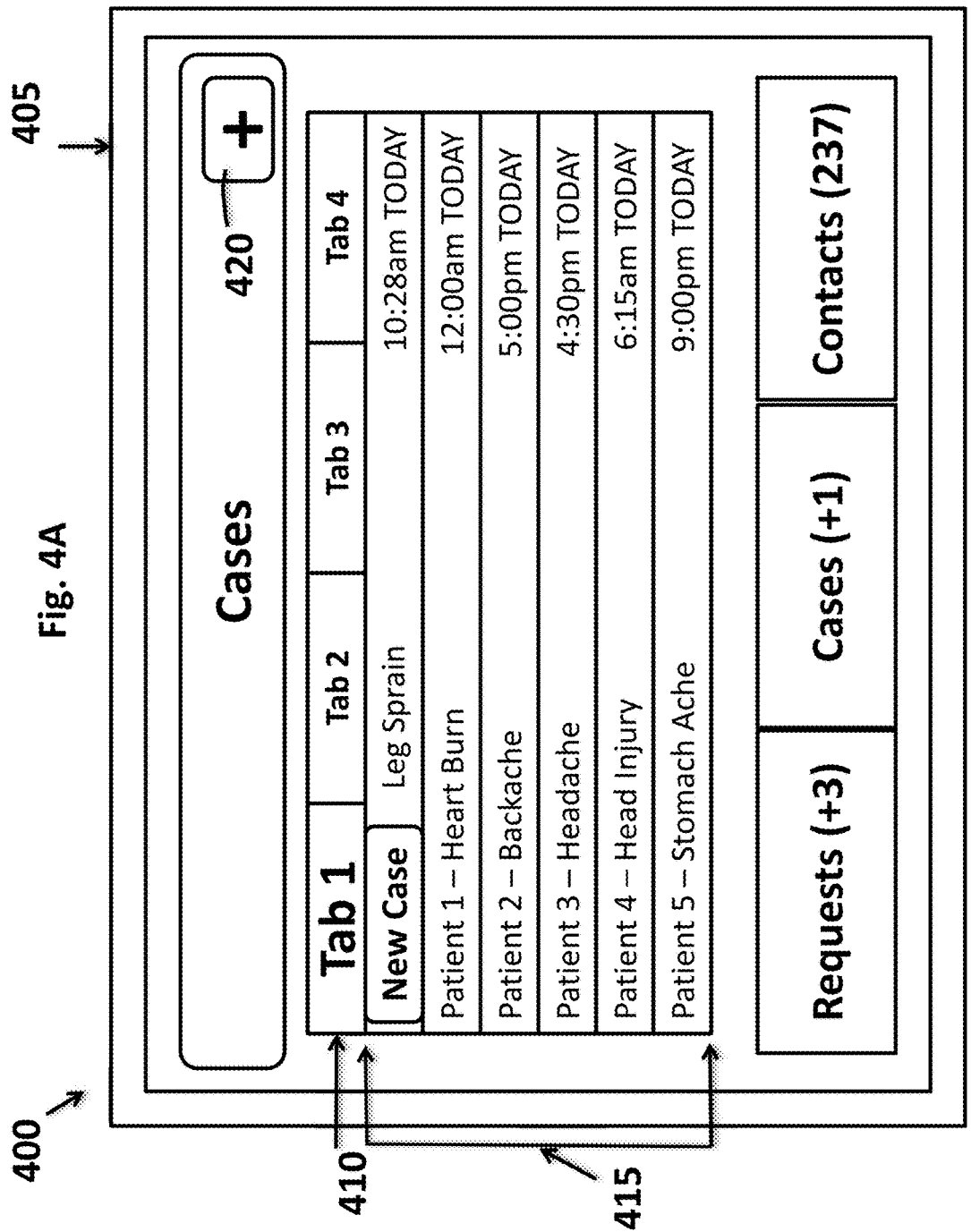

Furthermore, each of the mini panels 310-345 may provide the user of the device 300 with a "quick view" of the various functionalities that the user may have access to. By clicking on one of the mini panels 310-345, the user may gain a detailed access to the functionality representing that mini panel. For example, by clicking the case work mini panel 310, the user may access a list of all or a subset of cases that the user may be currently handling, cases that the user may have handled in the past, as well as all new cases that the user is not currently handling but may have been requested to take on. In some embodiments, from within the case work mini panel 310, the user may have the ability to sort cases in lists within different tabs for ease of access. For example, in those embodiments, all cases being currently handled may be displayed under one tab, while cases handled in the past may be displayed under another tab, and so on. In other embodiments, other sorting mechanisms (such as, sort by patient, illness, date, type of case, etc.) to sort the cases may be used. In at least some other embodiments, users may also have an ability to view a subset of cases, while hiding another subset of cases within the case work mini panel 310. In some embodiments, the case work mini panel 310 may also allow the user to create new cases, manage existing cases, and delete cases, if needed, as well as to customize the attributes of a case to be displayed in list form. Other features, described below, may also be accessible from within the case work mini panel 310. An illustrative example of what the user may see, in at least some embodiments, upon clicking the case work mini panel 310 is shown in FIG. 4A.

Similarly, by clicking the status mini panel 315, the user can prioritize communications. Specifically, from within the status mini panel 315, the user may set a receiver priority for the device 300 to prioritize the incoming communications. As will be described further below, from the status mini panel 315, the user may be able to define whether the user is busy, available, has a limited availability, or would not like to be disturbed at all. The currently set receiver priority status of the user may be viewed on the status mini panel 315 of the overall panel 305 for user's quick reference. For example, by looking at the status mini panel 315 on the overall panel 305 in FIG. 3, the user may quickly tell that the user's receiver priority is "busy." Additional details of prioritizing communications is discussed in FIGS. 8-10B below.

With respect to the notifications mini panel 320, by clicking on the notifications mini panel, the user may access all the notifications that the user may have received. The user may define within the notifications mini panel 320 whether to display only unread (e.g., unacknowledged) notifications, all notifications received (e.g., both read and unread), or notifications received, whether read or unread, within a certain time period. Also, in at least some embodiments, the user may define what kinds of notifications to receive. For example, in at least some embodiments, the user may select to receive notifications corresponding to requests for new cases, requests or updates on existing cases, requests to close cases, etc. and, at the same time, the user may select not to receive or mute notifications for certain other events.

Furthermore, the user may define whether to receive push notifications, receive notifications upon demand, or within a certain period. In at least some embodiments and as discussed below, when the notifications are received may depend upon the receiver priority and certain filters set within the status mini panel 315. For example, the manner in which, if at all, the notifications are received, displayed, and the user is alerted on the notifications mini panel 320 may correspond to the receiver priority defined by the user within the status mini panel 315. The user may also be able to define whether to receive an audible, visual, or tactile (e.g., vibratory) alert from the device 300 when the notifications are received. Additionally and similar to the status mini panel 315, the notifications mini panel 320 may also show, on the overall panel 305, the total number of notifications that the user may have received since the user last acknowledged or read the notifications. For example, in the present embodiment, by looking at the overall panel 305, the user may tell that the user has two unread notifications.

Referring still to FIG. 3, by clicking on the time log mini panel 325, the user may be able to enter, for every case worked on, the total time the user may have spent on that case, as well as provide a brief description of the kind of work done on that case. In at least some embodiments, the user may enable the medical application 250 to automatically calculate and enter the total time worked on a case by the user within the time log mini panel 325. In other embodiments, from within the time log mini panel 325, the user may establish a fixed period of time for each category of work to be performed. Additional features relating to keeping track of and entering time, as well as other time management features may be provided in the time log mini panel 325.

Similarly, by clicking on the profile mini panel 330, the user may define his/her own profile. For example, in at least some embodiments, the user may set its profile photo and make the photo visible to the user's contacts, set the user's birth date, or set other user identifying attributes or other preferences. Relatedly, by clicking the settings mini panel 335, the user may alter global settings impacting all of the features within the medical application 250. For example, the user may set his/her privacy settings, display settings, connectivity settings, etc., from within the settings mini panel 335.

Turning now to the summary mini panel 340, that panel may display, for user's reference, new requests on existing cases on a request mini panel 350, new case requests on a case request mini panel 355, and the total number of user's contacts on a contacts review mini panel 360. In at least some embodiments, the user may define (such as from within the settings mini panel 335) whether the summary mini panel 340 is to be a floating toolbar that may be visible as a collapsible bar from every page within the medical application 250 or a sticky toolbar that may be visible in expanded form from every page within the medical application. In other embodiments, the user may also be able to define what features the user may want to have on the summary mini panel 340. For example, in the present embodiment, the user has chosen to view the request mini panel 350, the case request mini panel 355, and the contacts review mini panel 360. In other embodiments, the user may choose other features to display on the summary mini panel 340.

Figure 5A:
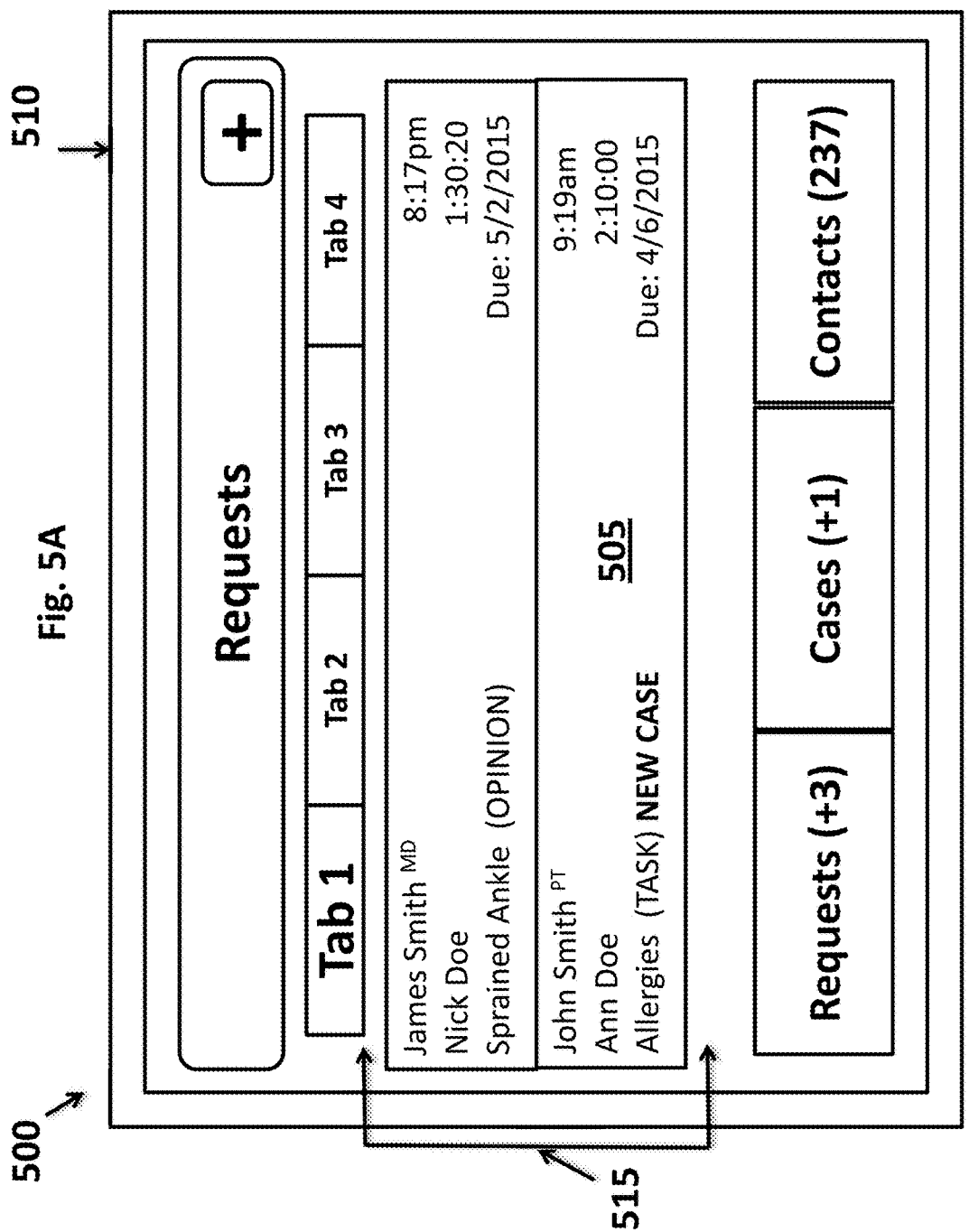

With respect to the features currently shown on the summary mini panel 340, by clicking on the request mini panel 350, the user may be shown a clickable list of all the received requests, as well as all other actions (such as, delete request, accept or deny request, go to the case for which the request pertains to, etc.) that the user may take for each of those requests. An illustrative example of what the user may see upon clicking the request mini panel 350 is shown in FIG. 5A. Similarly, clicking the case request mini panel 355 may show the user all the new case requests that the user may have received, as well as various details pertaining to those requests. Finally, by clicking either the contacts review mini panel 360, or the contacts mini panel 345, the user may be able to view all of its contacts. The contacts within the contacts mini panel 345 may correspond to the user's contacts on the device 300 or alternatively, the user may have a separate set of the contacts for participants of the medical application 250.

It is to be understood that the features of the various mini panels 310-360 described above are merely exemplary. These features may vary depending upon the attributes desired by the user, and upon the specific application for which the device 300 may be used. Additionally, the placement, as well as the shape, form, look, feel, and layout of the various mini panels 310-360 within the overall panel 305 may vary from one embodiment to another. Furthermore, it is to be understood that the mini panels are described above from the standpoint of a medical application. In other embodiments, depending upon the application, the number and type of the mini panels 310-360 may vary, such that mini panels that may be more suitable for those applications may be used. Even other medical applications may have other or different types of mini panels, as may be deemed more suitable.

Turning now to FIGS. 4A-4D, illustrative block diagrams 400 showing steps to add a new case in a device 405 are shown, in accordance with at least some embodiments of the present disclosure. The device 400 is similar to the device 300, described above. A new case may be created by either the health care practitioner 105 or the caregivers 110-125 of FIG. 1. To create a new case, the user of the device 400 may first go to the overall panel 305 of FIG. 3 above and click the case work mini panel 310. Upon clicking the case work mini panel 310, as described in FIG. 3 above, a list of cases may be displayed. As specifically shown in FIG. 4A and described above, in at least some embodiments, the list of cases may be sorted out into various tabs 410 and each tab may have a scrollable list of various cases 415. Each case entry in the list of various cases 415 may provide a "quick view" reference of that case. For example, in at least some embodiments, each "quick view" reference may show whether the case is a new case or not (e.g., by prefixing the entry with the phrase "new case"), the name of the case, name of the patient, and the last time the case was accessed by any participant of the case. The participant need not always be the user of the device 405. Rather, in at least some embodiments, the participant may be any person having access to the medical application 250 and who may be linked to that case. In other embodiments, other or additional details may be shown on the "quick view" reference of each case.

To create a new case, the user clicks a new case button 420. While in the present embodiment, the new case button 420 has been shown via a "+" sign, this is merely exemplary.

Any text, symbol, or a combination thereof may be used to enable the user to create a new case. Furthermore, the placement of the new case button 420 may be changed, as desired, from one embodiment to another. After clicking the new case button 420, the user is directed to a new case panel 425 of FIG. 4B. Within the new case panel 425, the user may provide patient information 430, a case name 435, participants 440, and a description 445 of the newly created case.

With respect to the patient information 430, in at least some embodiments, the patient may be an existing patient with a new ailment, while in other embodiments, the patient may be new to the user. If the patient is an existing patient, the user may be able to find the patient's information from the user's contacts (e.g., from the contacts mini panel 345). If the patient is new or if the patient is an existing patient but does not have a record in the user's contacts, then a new patient entry may be created for that patient. To create a new patient entry, the user may create a patient profile by entering patient's identifying information, such as first name, middle name, last name, date of birth, an identification card that identifies the patient, and identification number on the identification card. Other types of identifying and demographic information about the patient may also be collected and stored in the patient profile. Furthermore, the user may add a photo, if available, of the patient, as well as include a scanned copy of the identification card. The user may also have the option to change the photo and re-scan the identification card or scan a new identification card. In at least some embodiments, the user may use a camera on the device 405 in order to take photos and scan the identification cards. In other embodiments, other mechanisms may be used. Furthermore, in at least some embodiments, the new patient profile may be automatically added to the user's contacts list on the device 405.

Upon choosing an existing patient profile or creating a new patient entry, the patient name or other information related to the patient may display within the patient information 430, as shown in FIG. 4C. After entering the patient information 430, the user enters the case name 435. The case name 435 may be a brief descriptive name co-relating with the ailment of the patient, or any other name that may suitably identify and distinguish this case from other cases. The case name 435 may be added by clicking within the case name 435 to display a keypad and typing in the case name.

Subsequent to entering the case name 435, the user may add any of the participants 440. As discussed above, the participants 440 may be another health care practitioner 105 or another caregiver(s) 110-125. Furthermore, similar to the patient, the participants 440 may or may not be in the user's contact list. If the participants 440 are on the user's contacts list, the contact information of those participants may be imported from the user's contacts list. If not, the user may create a new profile for the participants similar to the patient profile for new patients, described above. The new profile of the participants may be saved in the user's contact list for future reference and added to the participants 440. In at least some embodiments, the user may not know what participants may be needed on the new case. So, the user may skip assigning the participants 440 at the time of creating the case and add participants later on. In yet other embodiments, the user may not need any other participants on the case. In that case, the user may leave the participants 440 blank.

The user may also add the description 445, which may include adding a brief text note about the case, audio, video, photographs, or other attachments using various buttons on tab 450. Once all of the information is entered in the new patient panel 425, the user may click a create button 455 to create the new case. A confirmation 460 may be displayed to convey to the user that the case creation was successful, as shown in FIG. 4D. Once the new case is created, information about the new case may be shown in a new case entry 465 in the list of the cases 415. After creating the new case, the participants 440 may be sent a request to either accept or reject the case. Responding to a request of a new case is described in FIGS. 5A-5D below.

Turning now to FIGS. 5A-5D, illustrative block diagrams 500 showing steps for responding to a new case request 505 in a device 510 are shown, in accordance with at least some embodiments of the present disclosure. The device 510 is similar to the device 300. Further, as discussed above, when a new case is created, the participants 440 may be added to the new case. If the participants 440 are added, those participants may be sent a request regarding the new case. If the participants 440 have the medical application 250 installed on their device, then the participants may respond to the new case request 505, as described below. If the participants 440 do not have the medical application 250 installed on their device, the participants may still be able to respond to the new case request 505 via a web application or the participants may install an instance of the medical application 250 on their device and then respond to the new case request 505, as discussed below.

In at least some embodiments and referring specifically to FIG. 5A, the new case request 505 may be displayed within a list of requests 515. The new case request 505 may be identified by virtue of the highlighted phrase "new case." Further, in the list view, the new case request 505 may provide a "quick view" reference of the case. For example, in at least some embodiments, in the list view, the user may be able to see the name and title of the person (e.g., which one of the health care practitioner 105 or the caregivers 110-125) who sent the new case request 505, the name of the patient, as well as the case name and the type of request. The new case request 505 may also specify the due date by which the user of the device 510 is desired to either accept or deny the case, the time the request was received by the user of the device 500, and the total time worked on the case so far by all the participants combined. In other embodiments, other or additional details may be shown on the "quick view" reference of the new case request 505.

By clicking on the new case request 505 of FIG. 5A, the user is directed to the block diagram of FIG. 5B where the user may be shown a dialogue box 520 asking whether the user would accept the case or not. If the user clicks "no" in the dialogue box 520, then the case may not be added to the list of the cases 415 (discussed above in FIGS. 4A-4D) of the user and a notification may be sent to the person who sent the new case request 505. The user of the device 510 may have an option to add notes explaining the reason for rejecting the case. On the other hand, if the user accepts the case by clicking "yes" in the dialogue box 520, then the user is taken to the block diagram shown in FIG. 5C where additional details of the case are made visible to the user. For example, as shown in FIG. 5C, a notification area 525 may display notes 530 from the person who sent the request. Any videos or attachments, if added to the case would also be visible in the notification area 525. The user may review the notes 530 before deciding how to respond back.

Figure 5D:
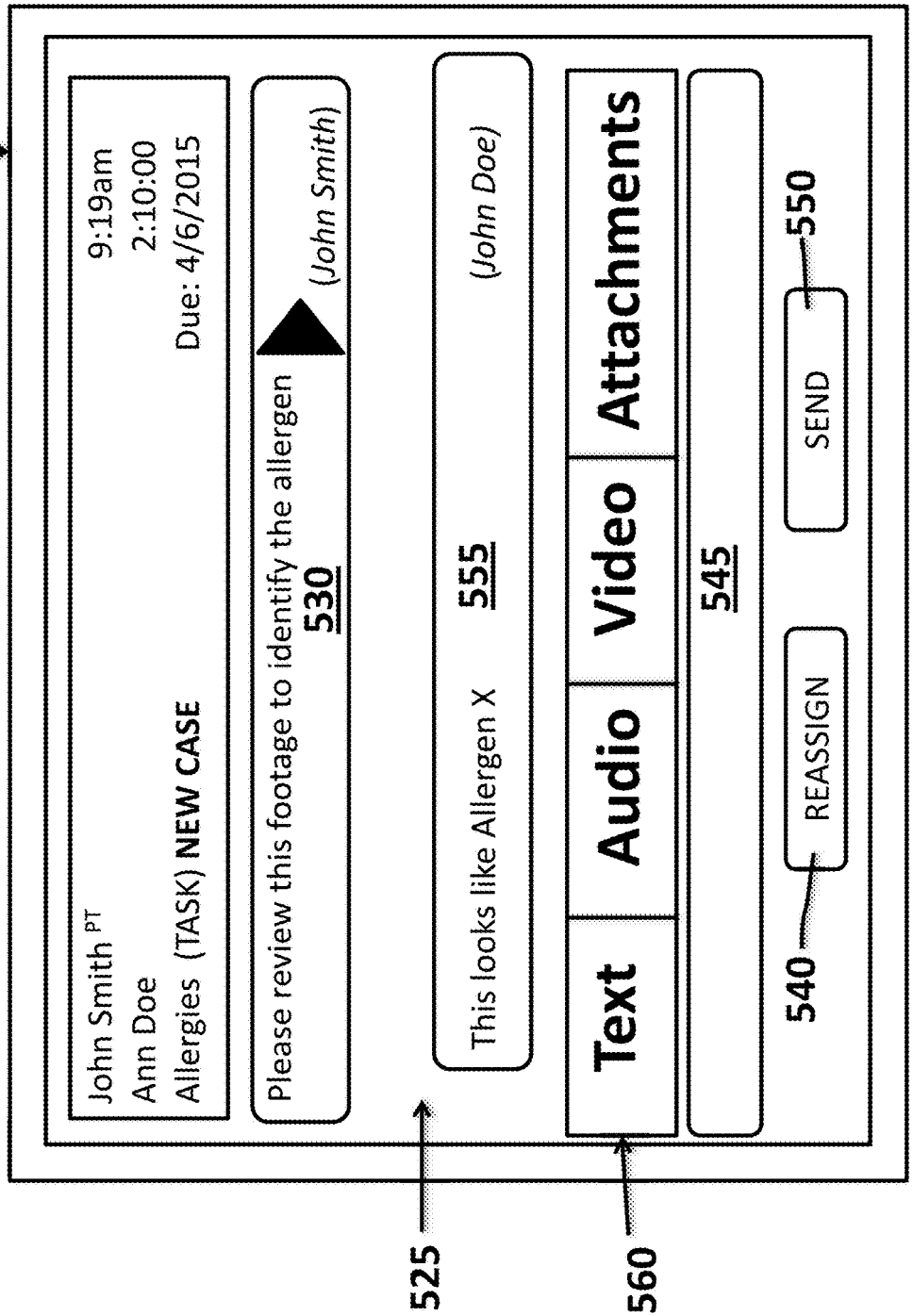

After reviewing the information within the notification area 525, the user may change his/her mind and still decide to reject the case by clicking on a reject button 535 or re-assign the case to another person who might be better suited to handle the case by clicking a re-assign button 540. If the user decides to keep the case, then the user may add any notes, thoughts, or comments in text area 545. Once information is added within the text area 545, a send button 550, which is inoperative when the text area has no text, becomes operative. By pressing the send button 550, the text from the text area 535 is transferred to the notification area 525 as user notes 555, shown in FIG. 5D, and an automatic notification may be sent to the person who had originally sent the request. In addition to text, the user may also add audio, video, attach photographs or documents, using a tab 560, in responding to the new case request 505. Furthermore, once the user has responded to the new case request 505, the user may not reject the case. However, as shown in FIG. 5D, the user may still re-assign the case, if needed.

Figure 6A:
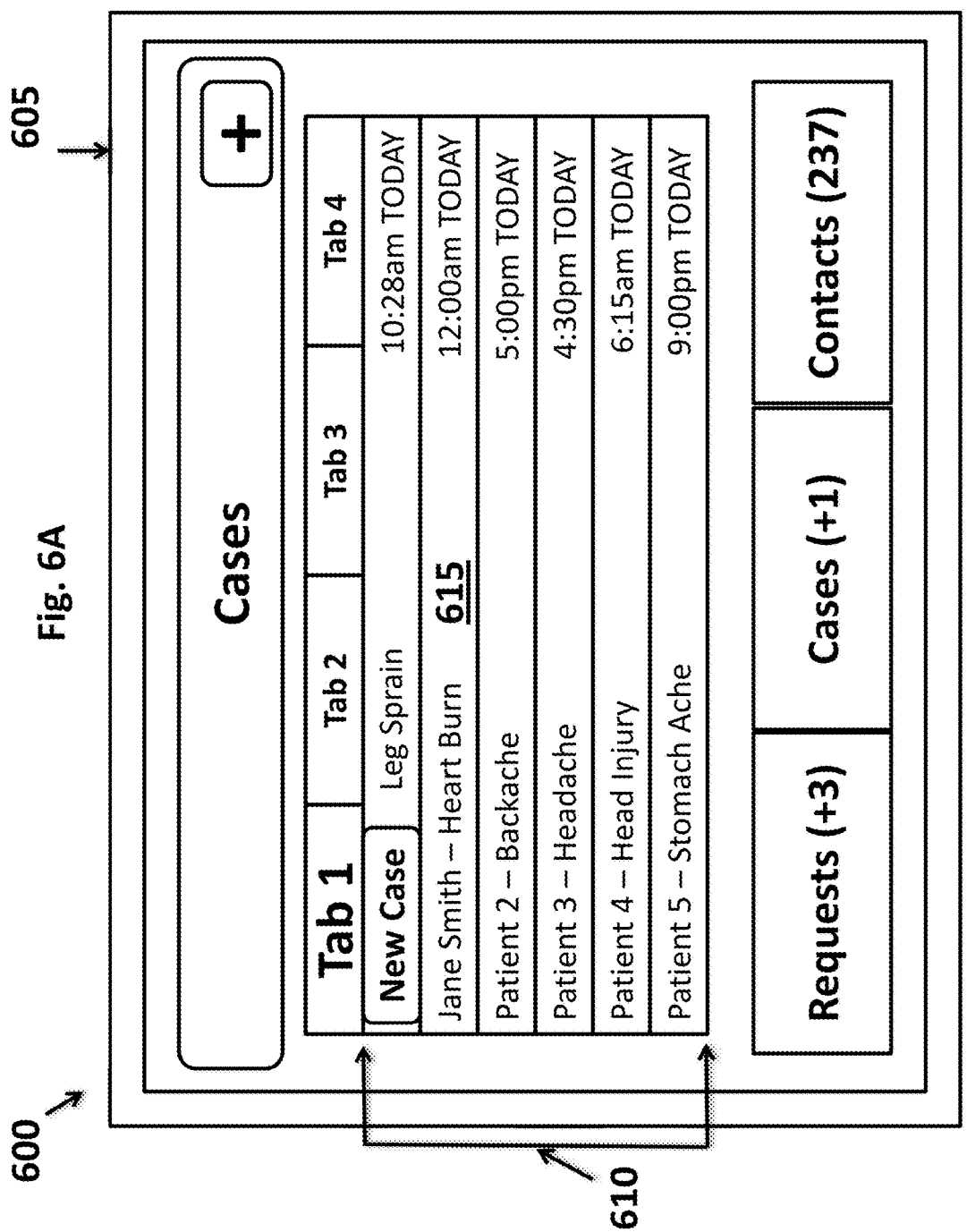
Figure 6D:
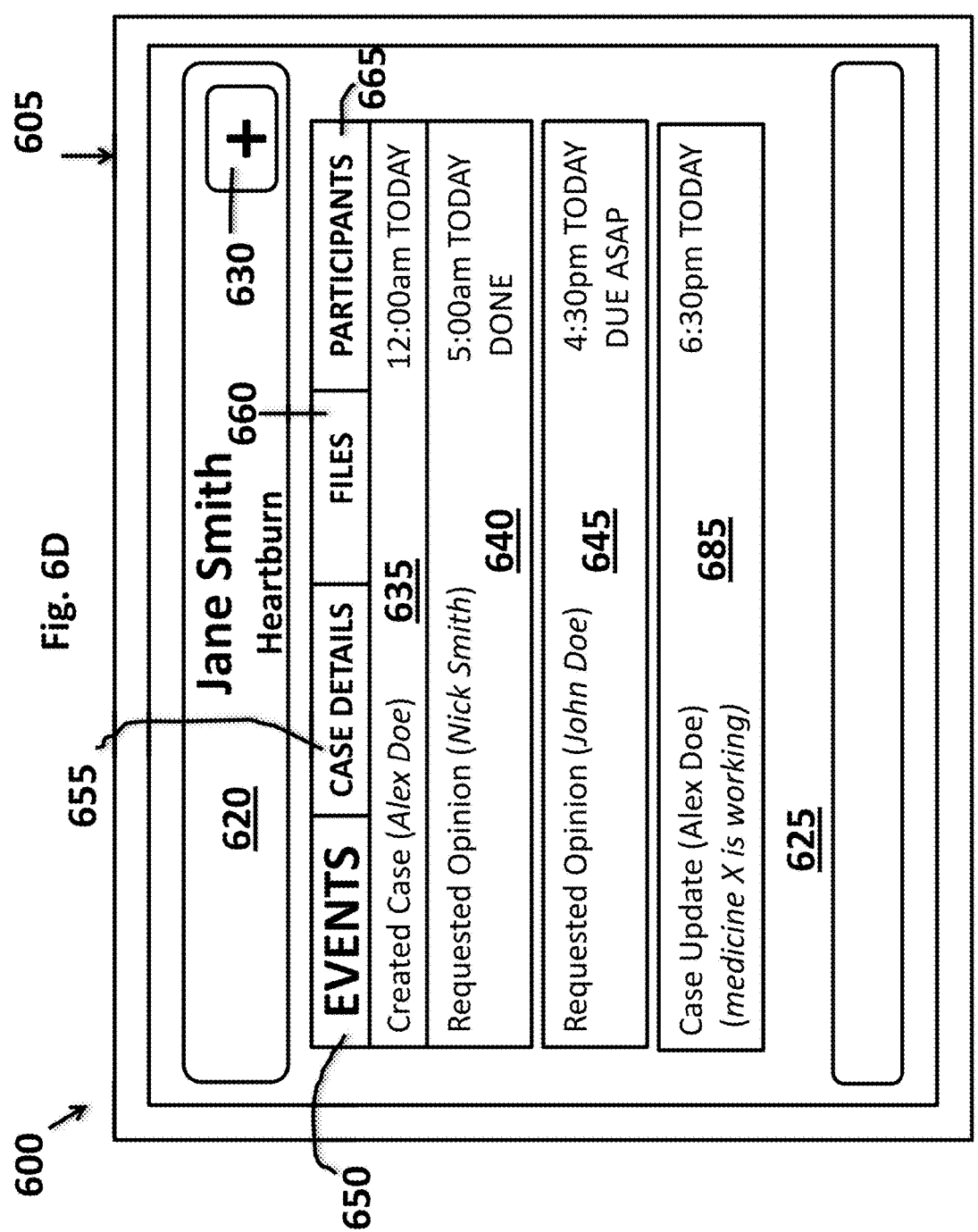

Turning now to FIGS. 6A-6D, illustrative block diagrams 600 showing a case management feature of the medical application 250 installed on a device 605 is shown, in accordance with at least some embodiments of the present disclosure. Specifically, FIGS. 6A-6D show adding an update to an existing case within the medical application 250. Referring particularly to FIG. 6A, to add an update to an existing case (e.g., such as to a case created in FIGS. 4A-4D), a user of the device 605 clicks on the case work mini panel 310 of FIG. 3 to see a list of cases 610. The list of cases 610 is similar to the list of cases 415 described in FIG. 4A above. To add an update to one of the cases shown within the list of cases 610, the user clicks on the desired case. For example, as shown in FIG. 6A, the user may desire to add an update to case 615. To add an update to the case 615, the user clicks on the case 615 to view the details of that case, as shown in FIG. 6B.

Referring to FIG. 6B now, the details of the case 615 may include the name of the case in a case name area 620, a record of the case in a case record area 625 organized under various tabs, and an update/request button 630 to add new updates or requests to the case. The case record area 625 may include a list of updates and requests in the case 615. For example, as shown, the case record area 625 of the case 615 may include a case update 635, and two case requests 640 and 645, all displayed under an events tab 650. Additional details (e.g., details of what the case is about, any medicines prescribed in the case, list of immunizations, etc.) of the case 610 may be found under a case detail tab 655 of the case record area 625. Any images, videos, documents, or other types of files may be organized under a files tab 660, while a participants tab 665 may include a list of participants of the case 615. In other embodiments, different or additional tabs may be provided depending upon the use desired.

Furthermore, in at least some embodiments, each of the case update 635 and the case requests 640-645 under the events tab 650 in the case record area 625 may provide a "quick view" reference of the update or the request. For example, in at least some embodiments and as shown, for each entry in the case record area 625, a type of the update or request (e.g., "created case" for the case update 635 and "requested opinion" for the requests 640-645) may be shown. Each entry may also show a name of the person who created the update or request, if the request was sent out to another person, the name of that person, deadline for responding to the request, if applicable, etc. In other embodiments, other details within each update or request may be shown for quick reference. Furthermore, additional details may be available for the user's viewing by accessing a particular update or request (e.g., by clicking on that update or request).

To add a new update to the case 615, the user clicks on the update/request button 630. Upon clicking the update/request button 630, the user is directed to a dialogue box 670 of FIG. 6C. As shown in FIG. 6C, the dialogue box 670 may include a first section 675 that may be used by the user to add a new update to the case 615. The dialogue box 670 may also include a second section 680, which as described below, may be used by the user to add a new request to the case 615. As used herein, an "update" or case update" to a case may include any notes, summaries, documents, images, videos, or other information that may be added to document the happenings in the case or to otherwise serve as reminders, but not designed to be transmitted to other users or solicit any action. A "request," on the other hand, may include any communications that are designed to be exchanged with other users and may or may not solicit any action from the users.

Thus, the user of the device 605 may add an update to the case 615 by clicking anywhere within the first section 675 of the dialogue box 670. Then, the user may document the update within the first section 675 by way of one or more of text, audio, video, photographs, or attachments. Once the user has finished compiling the update within the first section 675, the user has the option of saving the update. If saved, the newly added update is added to the case record area 625 under the events tab 650 as a new entry 685, shown in FIG. 6D. Furthermore, although not shown, in at least some embodiments, the user may be able to edit or delete the update shown in the new entry 685. Additional new updates may be added in a similar way by clicking on the update/request button 630.

Figure 7A:
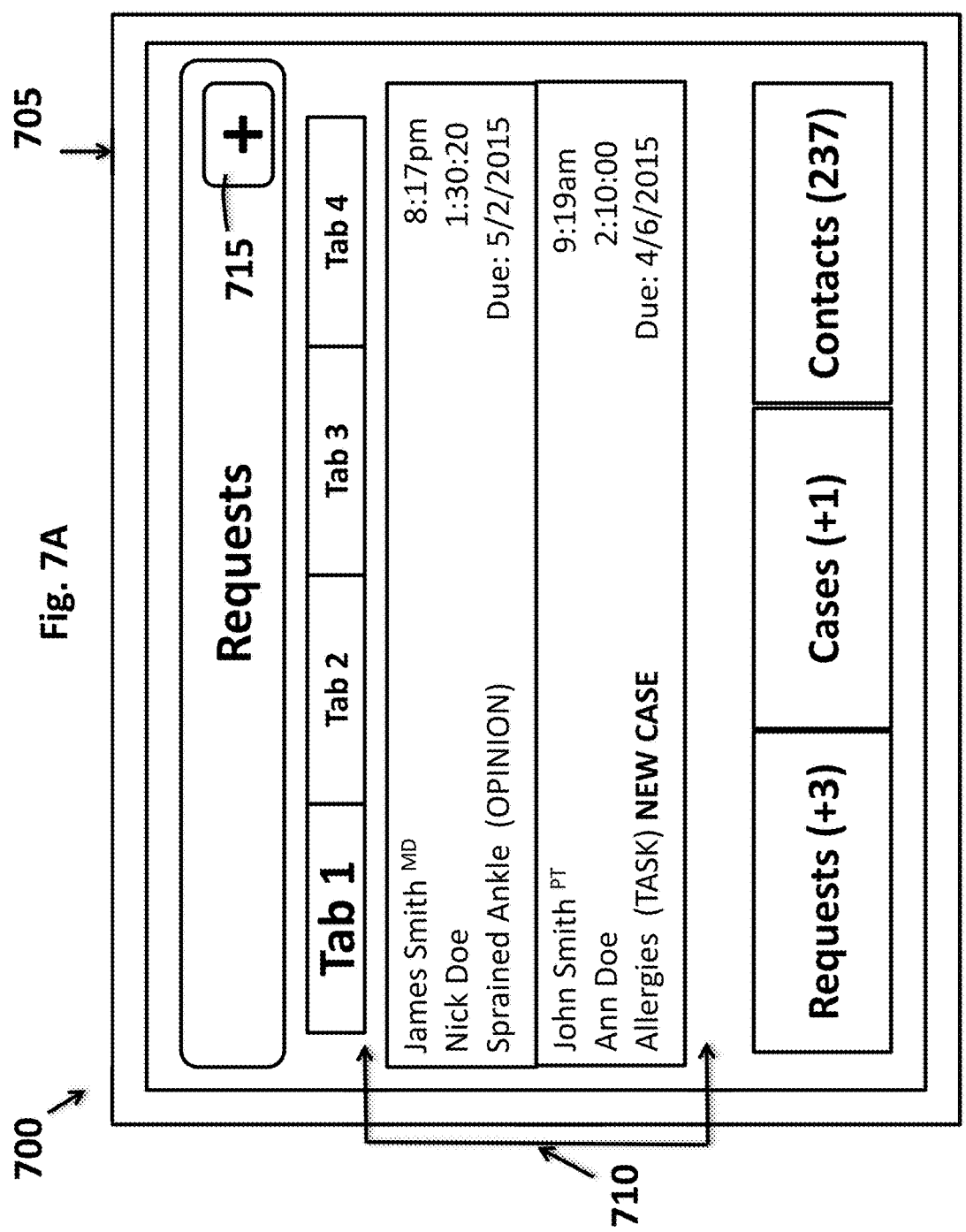

Referring now to FIGS. 7A-7D, illustrative block diagrams 700 showing another case management feature of the medical application 250 installed on a device 705 is shown, in accordance with at least some embodiments of the present disclosure. Specifically, FIGS. 7A-7D illustrate adding a new request to an existing case. A new request to an existing case may be added in at least two ways. The first way is shown in FIGS. 7A-7D. Referring specifically to FIG. 7A, a list of requests 710, organized under various tabs, may be accessed from the request mini panel 350 on the summary mini panel 340, described in FIG. 3 above. Each request within the scrollable list of requests 710 may provide a "quick view" reference of the request to the user. In at least some embodiments, the quick reference view may include the name of the person from which a request is received, the name of the patient, case name, the type of request, the due date for responding to the request, and a date/time stamp of the request. In other embodiments, other or different details may be provided in the "quick view" reference of a request.

A new request to an existing case may be added by clicking on a request button 715. By clicking on the request button 715, a new request panel 720, shown in FIG. 7B, is opened to add a new request. The new request panel 720 includes a recipient field 725 to add the recipient of the new request, a case select field 730 to identify the case against which the new request is to be sent, and a request type field 735 to identify the type of the new request. With respect to the recipient field 725, the user may either type in the name of the recipient or click on an add recipient button 740 to select a recipient from a list. The recipient may be either a person whose information is stored within the contacts list of the device 705 or a person whose information is not stored within the contacts list. If the recipient is a person whose information is stored within the contacts list, then the user may select the name of that person from the contacts list to add to the recipient field 725.

On the other hand, if the recipient is a person whose information is not stored within the contacts list of the device 705, then the user may create (e.g., import) a new contact for the recipient by accessing a new contact panel from within the contacts list. In at least some embodiments, the new contact may be created (or imported) by adding the first and last name of the recipient, the type of practitioner that the recipient is (e.g., MD, PT, RN, NP, etc.), the specialty of that recipient (e.g., internal medicine, ophthalmology, pediatric, etc.), and the location of the recipient (e.g., city, state, and country). In other embodiments, additional or other details may be added while creating or importing a new contact. After creating or importing a new contact for the recipient, the medical application 250 on the device 705 may determine whether the recipient has an instance of the medical application installed on their device or not. If the medical application 250 on the device 705 determines that the recipient does not have an instance of the medical application installed on their device, then the user may still send a new request to the recipient, but along with an invitation to install an instance of the medical application of their device.

Thus, the name of the recipient may be added to the recipient field 725 either from the existing contacts list or a newly created or imported contact. After adding the recipient name, the user adds the name of the case in the case select field 730. By clicking within the case select field 730, the user may be able to either simply type in the case name, if known, select from an existing list of cases or create a new case. If the user decides to create a new case, the user may be directed to the panels described in FIGS. 4A-4D above in order to create the new case.

Once the case name is selected, the user identifies the type of request in the request type field 735. In at least some embodiments, the request may be any one of four types, namely, a task, an approval, a for-your-information, or an opinion. A task request may be a task that the user may want the recipient to perform. For example, a task request may ask the recipient to run certain laboratory tests, prescribe medications, talk to someone, etc. By an approval request, the user may seek approval for something from the recipient. For example, the user may seek approval from the recipient to refer a patient to another specialist, approval to perform certain tests, etc. An opinion request may seek the recipient's opinion. For example, the user may forward certain test results, photos, videos, audio, etc., to the recipient to seek the recipient's opinion on an issue. A for-your-information request may be merely an update in the case that the user may send to the recipient to keep the recipient abreast of any relevant developments in the case. In other embodiments, other types of requests may be provided in addition to or instead of the request types described above.

Thus, depending upon the type of request that the user desires to send to the recipient identified in the recipient field 725, the user can select that type of request from the request type field 735. Upon selecting the proper request type, the user is directed to a prioritization panel 745, shown in FIG. 7C. Specifically, the prioritization panel 745 shows the details selected by the user in the new request panel 720 of FIG. 7B, as well as an urgency field 750 to indicate the transmitter priority of the request to the recipient, and a due date field 755 to indicate the date by which the recipient is to respond back to the user.

Within the urgency field 750, in at least some embodiments, the user may select any one of three types of transmitter priorities, namely, normal, urgent, or critical. A normal request may seek a response from the recipient anytime before the due date mentioned in the due date field 755, an urgent request may seek a quicker turn-around time from the recipient, while a critical request may require a response as soon as possible from the recipient. In at least some embodiments, the type of transmitter priority may also be indicated by the due date mentioned in the due date field 755. For example, within the due date field 755, the user may solicit a response from the recipient within a day, as soon as possible, set a custom due date, or set no due date at all.

Upon selecting the transmitter priority and the due date of the request, the user may add any notes to the request in a note field 760. Clicking within the note field 760 takes the user to a finalize request panel 765, shown in FIG. 7D. Specifically, the finalize request panel 765 shows all of the information added by the user in the new request panel 720 and the prioritization panel 745. Additionally, the finalize request panel 765 expands the note field 760 to enable the user to add any notes. The user may add text, audio, video, photographs, or any other attachments to the note field 760. Once any desired notes are added, the user may click on a send button 770 to send the request to the recipient identified in the recipient field 725. If the medical application 250 had identified that the recipient did not have an instance of the medical application 250 on their device, an invitation to install the medical application is sent along with the request.

The recipient upon receiving the invitation to install the medical application 250 on their device may either (a) install the medical application to view and respond to the request; (b) sign in to the medical application, if the recipient already has the medical application installed, to view and respond to the request; or (c) view the request on a web application that does not require the recipient to install the medical application on their device.

As discussed above, the user of the device 700 may send a request in two ways. The first way is as described above in FIGS. 7A-7D. The second way is substantially similar to adding a new update to an existing case, as described in FIGS. 6A-6D. Particularly, to add a request to an existing case, the user of the device 705 may access the list of cases 610 by clicking on the case work mini panel 310. From the list of cases 610, the user may select a case to which a request is to be added. Upon selecting the case, the user may click on the update/request button 630 to see the dialogue box 670. As discussed above, the first section 675 of the dialogue box 670 may be used to add an update to the case, while the second section 680 may be used to add a request to the case. In at least some embodiments, upon clicking in the second section 680, the user may be directed to the new request panel 720 of FIG. 7B and then the user may add a request, as described above with respect to FIGS. 7B-7D.

Figure 8:
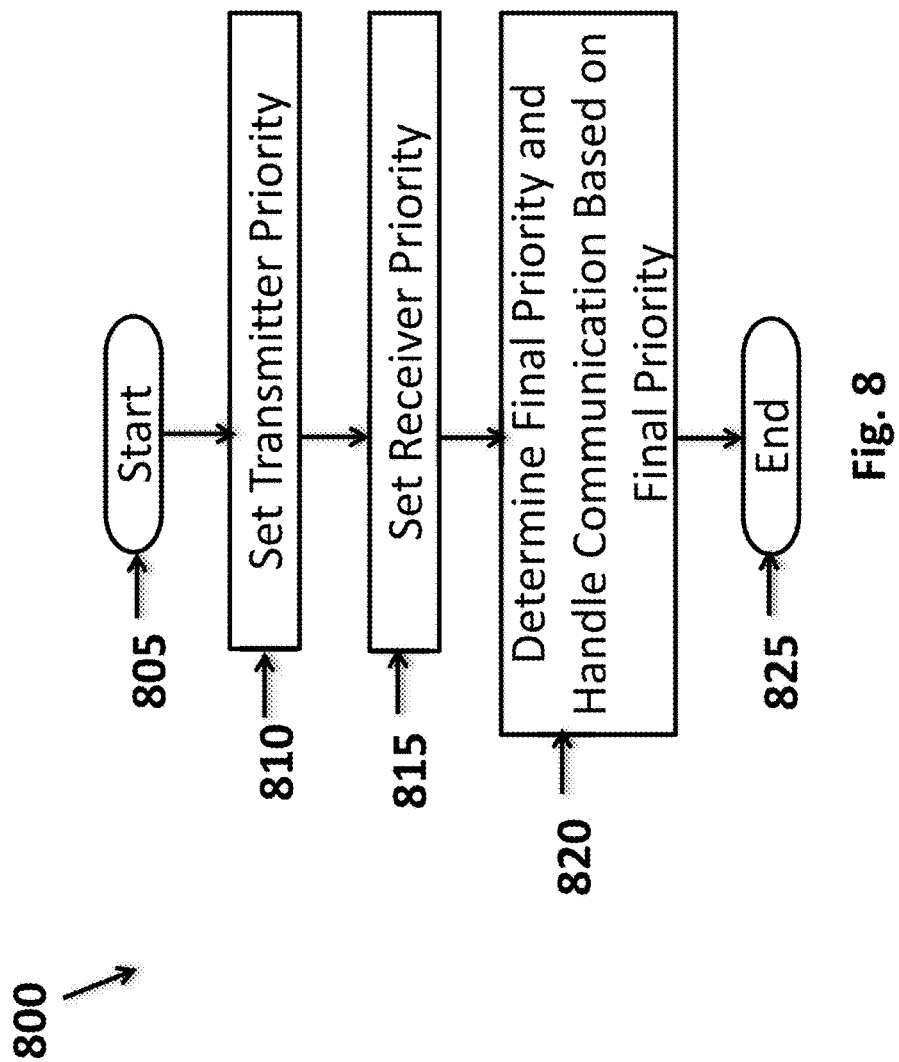
FIG. 8 is an illustrative flowchart outlining steps of prioritizing communications between the first device and the second device of FIG. 2 using the application software of FIG. 3, in accordance with at least some embodiments of the present disclosure.

Turning now to FIG. 8, an illustrative flowchart 800 outlining steps of prioritizing requests of the medical application 250 between a transmitter device (e.g., the first device 205 or the second device 210) and a receiver device (e.g., the first device or the second device) is shown, in accordance with at least some embodiments of the present disclosure. After starting at a step 805, the transmitter priority is set at a step 810. Specifically, transmitter priority is the priority or the type of urgency, discussed in FIGS. 7A-7D above, that a user of the transmitter device may set for each request that is sent out from the transmitter device. Again, as discussed above, the transmitter priority may be any one of three priorities, namely, normal, urgent, or critical. Next, at a step 815, the receiver device sets a receiver priority. By setting a receiver priority, a user of the receiver device may silence any or specific incoming phone calls, and mute alerts and notifications for a period of time. The receiver priorities that the user of the receiver device may choose from are shown in FIG. 9.

Referring specifically to FIG. 9 in conjunction with FIG. 8, the receiver priority on a device 900 (e.g., the receiver device) may be chosen from any of four receiver priorities 905, namely, available, limited availability, busy, or do not disturb, on a status panel 910 of the device. In other embodiments, other or additional receiver priorities may be made available on the device 900. The status panel 910 may be accessed from the status mini panel 315, discussed in FIG. 3 above. Furthermore, in at least some embodiments, the receiver priorities may be set such that with an "available" priority status, the user of the device 900 may choose to receive all incoming calls, alerts and notifications, while with a "limited availability" or a "busy" receiver priority, the user may choose to receive only certain calls, alerts, and notifications. Likewise, with a "do not disturb" receiver priority, the user may choose to silence all calls, alerts, and notifications. Additionally, within each of the receiver priorities, the user may set certain filters, such that despite a set receiver priority, the user may receive calls or requests from certain people, as well as receive notifications or alerts from certain requests (e.g., filter by the sender of the request, the type of request, the due date of the request, etc.). In other embodiments, the filters may be set to block certain calls and requests regardless of the set receiver priority. The filters may be set by highlighting one of the four receiver priorities 905 and clicking on a set filter button 915.

Figure 10A:
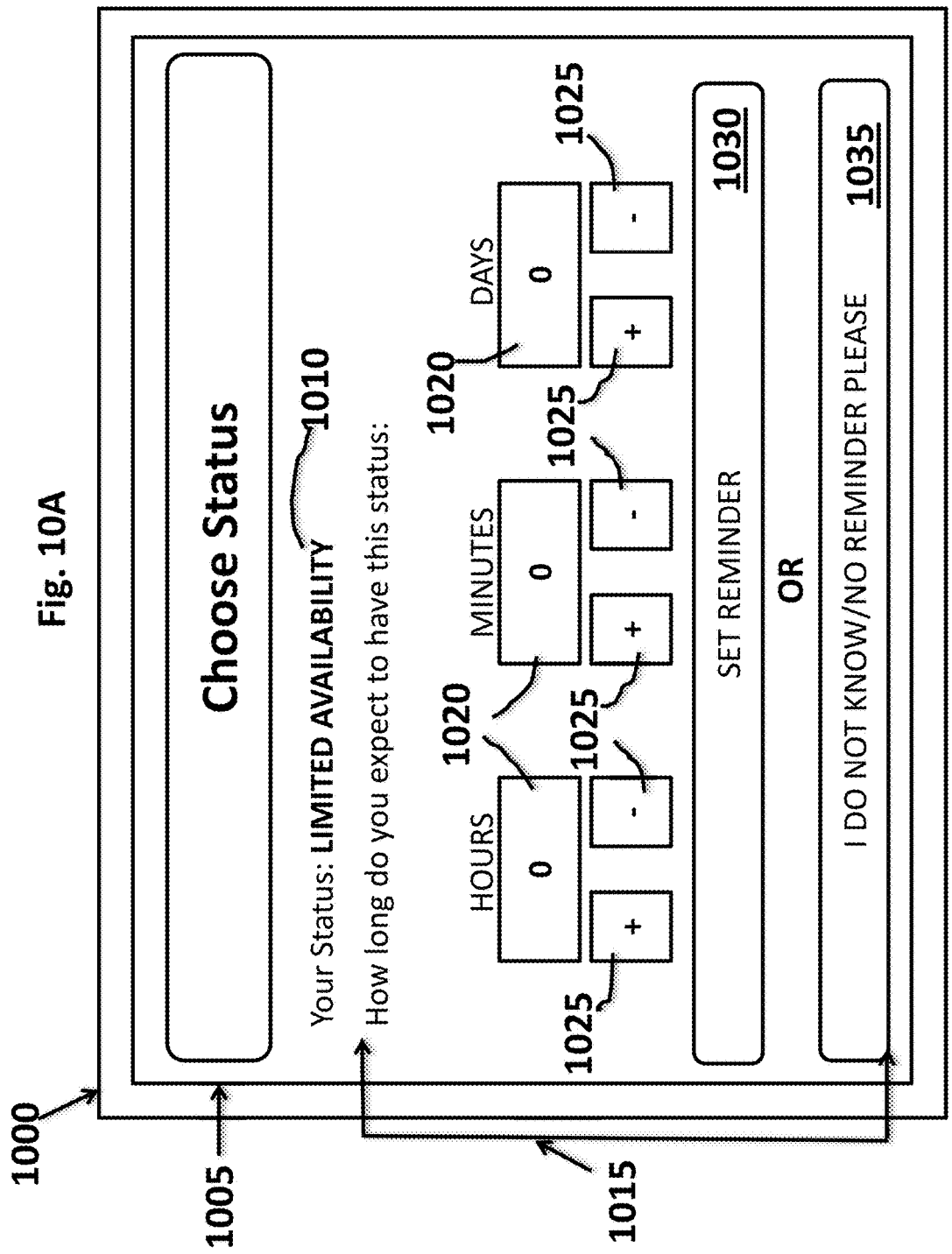
FIGS. 10A-10B are illustrative block diagrams showing one prioritizing feature of FIG. 9 in greater detail, in accordance with at least some embodiments of the present disclosure.
Figure 10B:
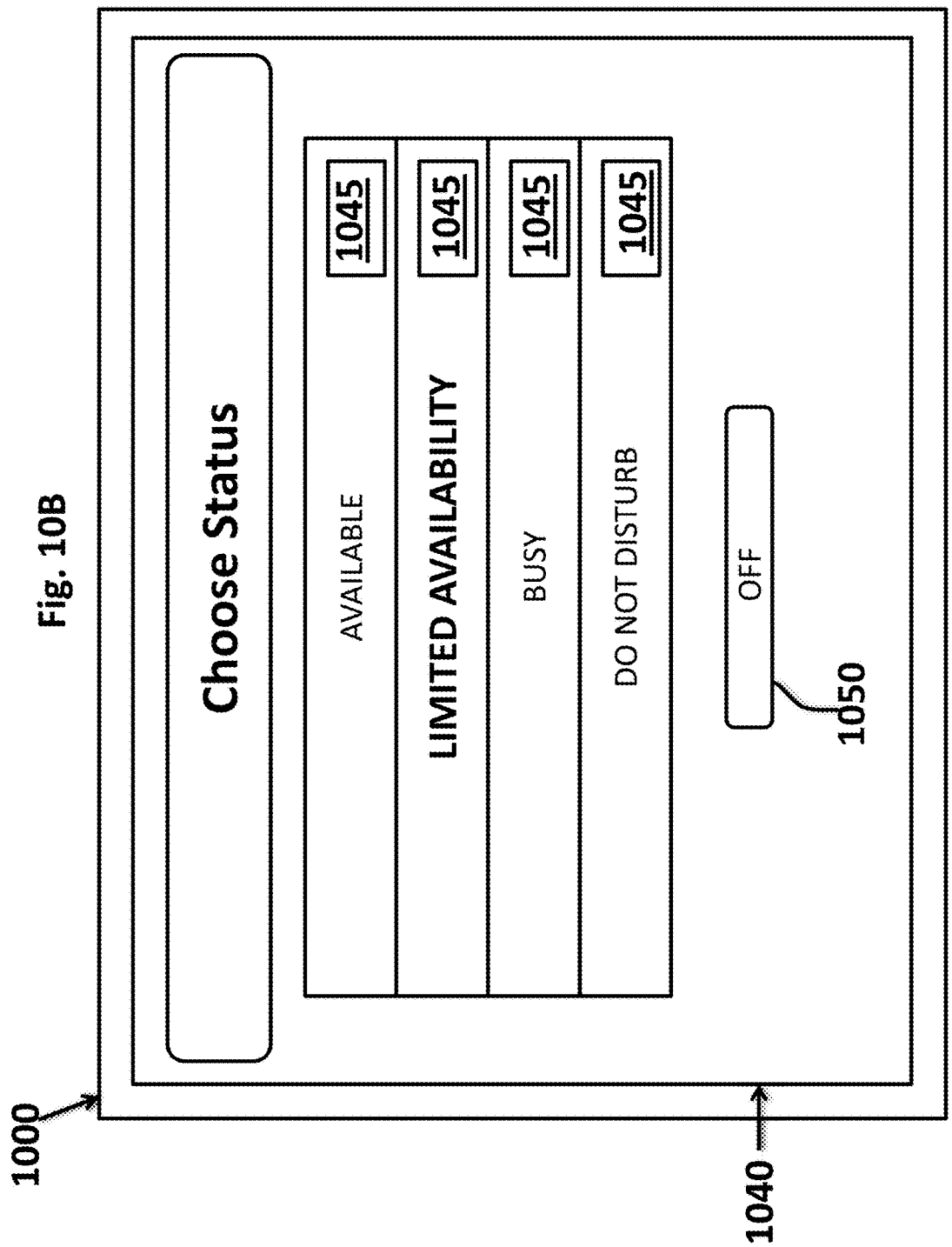

Moreover, for each of the receiver priorities, the user may set a reminder, by clicking on a set reminder button 920, to indicate a length of time for which a particular chosen receiver priority is to be set on the device 900. Again, the user of the device 900 may first highlight one of the four receiver priorities 905 that the user desires to set and then press the set reminder button 920 to set a reminder for the highlighted one of the four receiver priorities. An example of setting a reminder is shown in FIGS. 10A-10B. In at least some embodiments, the user may set both a reminder and one or more filters for each of the receiver priorities 905.

Referring now to FIGS. 10A-10B in conjunction with FIGS. 8 and 9, FIG. 10A shows an example of setting a reminder for a limited availability receiver priority on a device 1000. Notwithstanding the fact that FIGS. 10A-10B show setting a reminder for a limited availability receiver priority, similar reminders may be set for the other receiver priorities (e.g., available, busy, do not disturb) as well. As discussed above, to set a reminder for the limited availability receiver priority, the user first highlights the limited availability receiver priority on the status panel 910, and then clicks on the set reminder button 920. Upon clicking the set reminder button 920, the user is directed to a set reminder panel 1005 on the device 1000. The set reminder panel 1005 shows a currently selected receiver priority 1010, which lists the receiver priority highlighted on the status panel 910 and for which the user is setting a reminder on the set reminder panel 1005, and a timer area 1015 for setting a reminder for the currently selected receiver priority.

In at least some embodiments, the timer may be set by inputting the number of hours, minutes, and if needed, the number of days for which the device 1000 is to remain on the receiver priority indicated in the currently selected receiver priority 1010. Specifically, the number of hours, minutes, and days may be set by either clicking within text boxes 1020 to display a keypad and entering numbers on the keypad or by clicking on buttons 1025 to increase or decrease the value until a desired value is obtained within the text boxes 1020. Once the desired time values are entered within the text boxes 1020, the user may press button 1030 to set the reminder. In other embodiments, other mechanisms, such as voice prompts, to set a reminder may be used in addition to or instead of the mechanism discussed above. Furthermore, in at least some embodiments, the user may set the receiver priority shown in the currently selected receiver priority 1010 for an indefinite period by clicking on button 1035.

Once the timer for a priority status is set by either entering specific values for hours, minutes, and days in the text boxes 1020 and clicking the button 1030, or entering the priority status for an indefinite period by clicking the button 1035, the user may set various filters for the selected receiver priority 1010 on a status panel 1040 of FIG. 10B. The status panel 1040 is substantially similar to the status panel 910 of FIG. 9, discussed above. By clicking on button 1045 next to the selected receiver priority 1010, the user may be directed to a panel for setting various filters, as discussed above. Specifically, for each receiver priority, the user may select whether, in the chosen receiver priority, to receive alerts, notifications, or calls from one or more specific people, receive alerts and notifications regarding certain types of requests, from requests having certain type (e.g., normal, urgent, or critical) of the transmitter priority, or from requests having certain due dates. The filters may also be set to block certain calls, requests, or notifications. The status panel 1040 also shows the receiver priority for which the timer is set by highlighting that receiver priority on the status panel. Further, by clicking on a button 1050, the user may turn the reminder and/or the filters off.

Additionally, in at least some embodiments, the user of may set a default priority status (e.g., available). In those embodiments, the default priority status may be changed by specifically selecting a new priority status from the status panel 910 for a particular period of time and after the lapse of that time, the device 1000 may go back to the default priority status. In other embodiments, other priority features that may be deemed desirable may be set as well.

Returning back to FIG. 8, once the receiver priority is set at the step 815, the receiver device determines a final priority at a step 820. The final priority is based on a combination of the transmitter priority of the step 810 and the receiver priority of the step 815. In at least some embodiments, the final priority may be either a high priority or a low priority. With a high priority, the user may be alerted or notified about an incoming request, taking into account any filters that the user may have set. Relatedly, with a low priority, the user may not be alerted or notified about the request until such time as the reminder set in FIGS. 10A-10B has lapsed, again taking into account any filters that the user may have set.

Thus, for example, if the receiver priority at the step 815 has been set to a do not disturb, then in at least some embodiments, the final priority may be low and all requests from the transmitter device regardless of the transmitter priority may be ignored by the receiver device for a particular time period (e.g., for the reminder set in FIGS. 10A-10B), unless the user has set certain filters allowing certain calls, or notifications and alerts from certain requests. Similarly, if the receiver priority is busy, then in at least some embodiments, the final priority may be high if the transmitter priority is critical and the final priority may be low if the transmitter priority is urgent or normal. For a limited availability receiver priority, in at least some embodiments, the final priority may be high for both critical and urgent types of transmitter priorities, while the final priority may be low for normal types of transmitter priorities. Finally, with an available receiver priority, the final priority may be high such that calls from all callers may come through, as well as notifications and alerts from all requests, regardless of the type of request or the transmitter priority of that request, may be delivered. Again, the final priority may take into account any filters that the user may have set in deciding how to handle calls and requests with busy, limited availability, and available receiver priorities.

Thus, at the step 820, the receiver device determines the final priority by taking into consideration the transmitter priority and the receiver priority. After determining the final priority, the receiver device may either silence calls, ignore calls, or direct calls automatically to voicemail. Similarly, based upon the final priority, the receiver device may silence alerts and notifications or, in other words, the receiver device may not give out any audible, visual, or tactile indications of the request until the currently set priority status on the receiver device has expired. In other embodiments, other options to handle incoming calls and requests based upon the final priority may be provided. The process then ends at a step 825.

The medical application 250, therefore, provides a variety of beneficial features. For example, the medical application 250 permits case creation and access, such that users have the ability to quickly create a new case, as well as access all cases in which the user is a participant. The medical application 250 also allows users to easily add participants to a case. Generally speaking, participants may be added to either share or gather information related to a particular case, thereby allowing convenient, timely, and efficient data flow between groups of people involved in a particular case. Participants may either have a pre-existing relationship with other participants on a case or the participants may be new to the case. Similarly, regardless of whether a particular participant is using the medical application or not, features of the medical application permit the participants to be involved in a case, such as, by using a web application. In that regard, the medical application 250 allows universal access such that users who may not have the medical application installed on their hand-held devices may still access the medical application and participate in rendering care to patients. New participants may be easily invited by sending them a uniform resource identifier (e.g., a uniform resource locator, also known as web link) to a case on their electronic mail address or on a phone number of a smart computing device.

The medical application 250 further enables communications between participants to be simply and deliberately documented and recorded for future reference and retrieval. Communications may be facilitated either between two participants or between a group of participants. Furthermore, communications may occur in any of a variety of ways (e.g., calls, text messaging, instant messaging, etc.) and each piece of communication may be automatically documented by a date and time stamp. Moreover the medical application 250 enables versatile communications in that each communication that is sent or received may include photos, text, audio, video, other attachments, or any combination thereof. In at least some embodiments, the medical application 250 may also have a geo-position feature, which documents the location of each case. By virtue of using the geo-position feature, the medical application 250 may determine the location(s) of where patient encounters occur and utilize local services, local hospitals, local partnerships, etc. to deliver efficient, effective, and robust care to the patients even when the patients are away from their primary locale.

Additionally, the medical application 250 allows for communications from multiple resources and people to be appropriately prioritized. Such prioritizations allow for timely, focused interactions that improve and expedite care. In sum, the medical application 250 improves the quality, efficiency, and timeliness of medical decisions by giving a health care practitioner (e.g., the health care practitioner 105) access to remote experts (e.g., the caregivers 110-125) for facilitating care of the patients (e.g., the patients 130-140) in a more effective and collaborative way.

Figure 11:
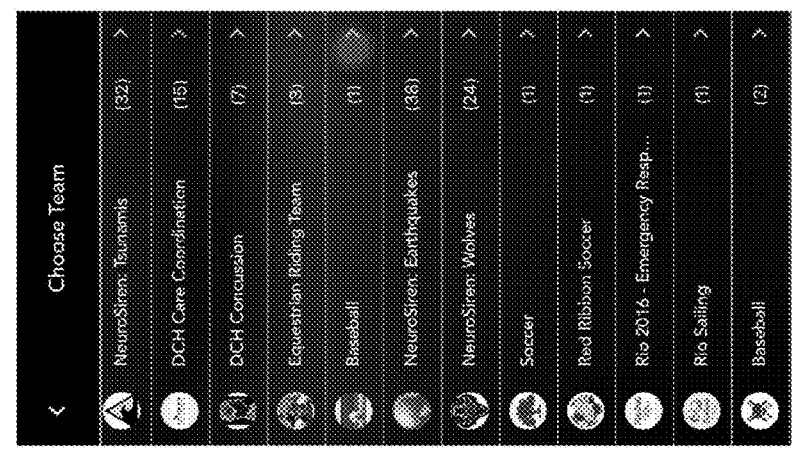
FIG. 11 depicts a team selection screen 1100 in accordance with an illustrative embodiment.

In addition to prioritizing individual users, a user is also able to prioritize groups of individuals such as entire team medical staffs. For example, a given surgeon may oversee players on both the Miami Soccer team and the Ohio State Tennis team. The surgeon can prioritize communications received from, for example, the Miami Soccer medical team over the Ohio State Tennis medical team. This prioritization of a medical team can be for a specified duration of time, or the surgeon can manually adjust the prioritization. As another example, the surgeon may oversee athletes from the Miami Marlins baseball team, and the Marlins may have a game on a Thursday night that starts at 6:00 pm. The surgeon can prioritize any communications received from the Miami Marlins medical team on Thursday night, and the prioritization can be set to a duration that covers a portion or all of the game. As a result, if a Miami Marlins player is injured during the game and the Marlins medical team reaches out to the surgeon, the received message will be prioritized over messages received from any other medical teams and/or individuals during the game. FIG. 11 depicts a team selection screen 1100 in accordance with an illustrative embodiment. From the team selection screen 1100, a user can select a given team and set that team's priority to high such that alerts/messages received from the given team have priority over alerts/messages received from other teams.

Figure 12:
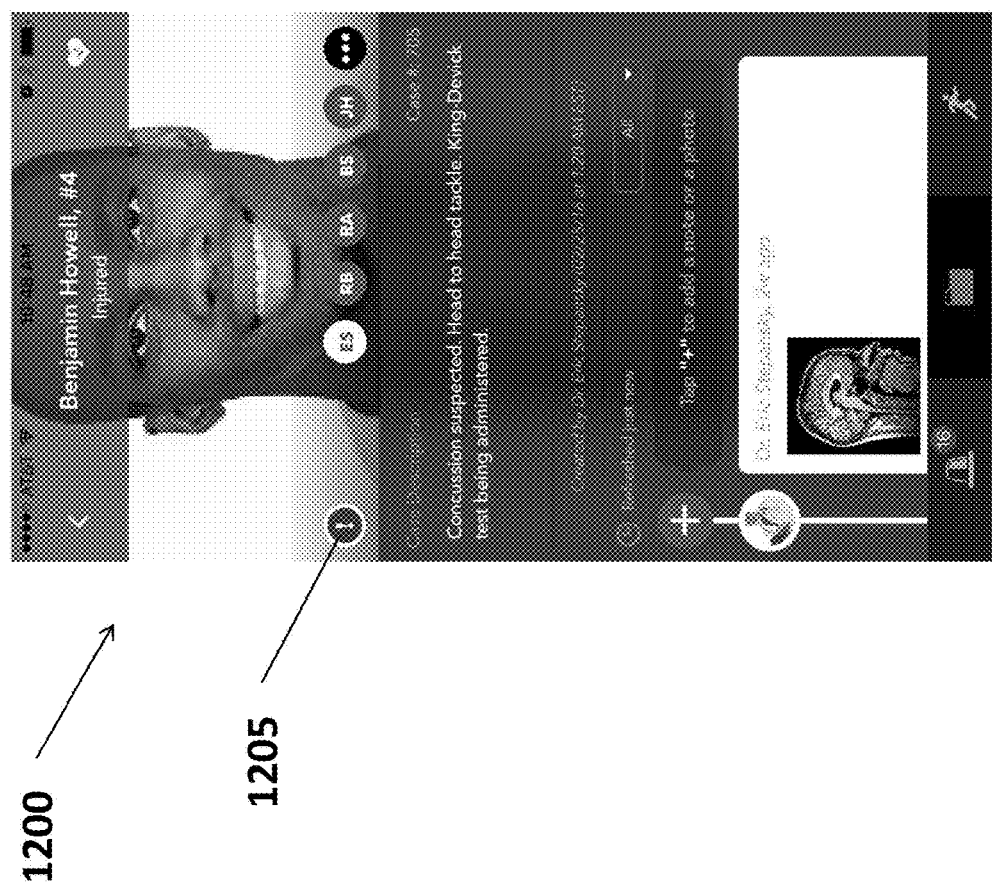
FIG. 12 is a screen shot depicting Transmitter initiated prioritization of a case in accordance with an illustrative embodiment.
Figure 13:
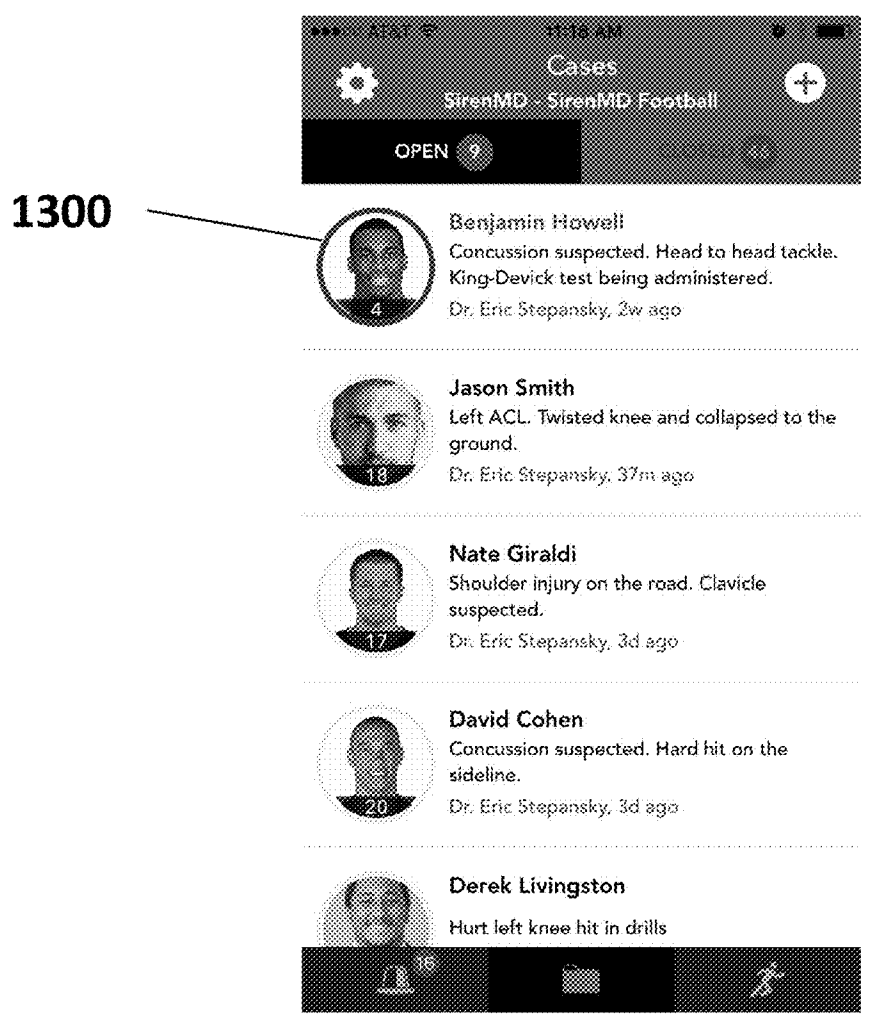

FIG. 12 is a screen shot 1200 depicting Transmitter initiated prioritization of a case in accordance with an illustrative embodiment. A button 1205, which is represented by an exclamation point, can be used to specify a given case as urgent, or high priority by a user. Upon activation of the high priority status for a given case, all caregivers who are included on that given case will all view this case as urgent. FIG. 13 depicts a case list of a caregiver associated with the case from FIG. 12, in accordance with an illustrative embodiment. As shown in FIG. 13, the high priority case 1300 is at the top of the list of the caregiver's cases and is highlighted to differentiate it from non-urgent matters.

Figure 14:
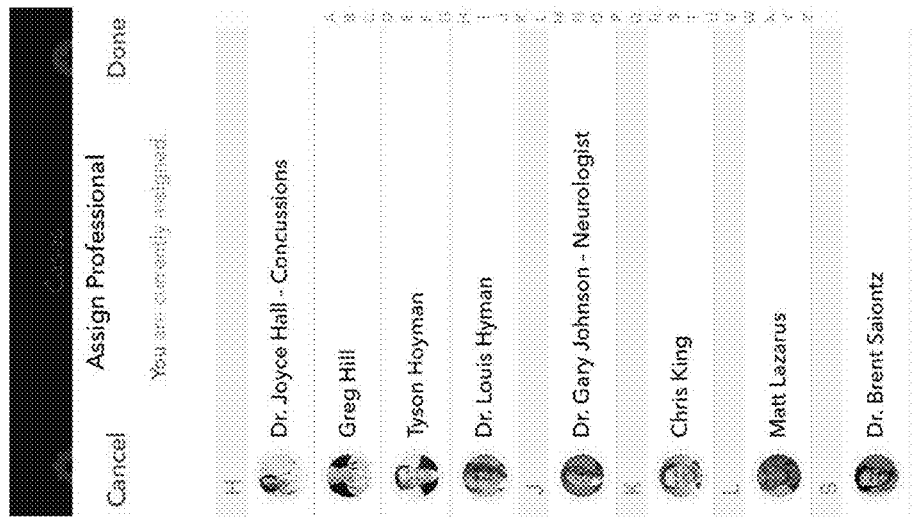
FIG. 14 depicts a caregiver assignment screen in accordance with an illustrative embodiment.

FIG. 14 depicts a caregiver assignment screen 1400 in accordance with an illustrative embodiment. A user can access the caregiver assignment screen 1400 to assign professionals to a given case. For example, a lead team doctor may assign a neurologist to a concussion case. Upon being assigned the case, the case details will be provided to the neurosurgeon through the application, and the neurosurgeon will be able to view the priority of the case as discussed above with reference to FIG. 13.

As discussed throughout, a number of different permutations can be used for the prioritization embodiments described herein. For example, in a first scenario, a transmitter (user) and receiver (user) can both indicate that a first case is not high priority (such an indication can be made by failing to actually specify that the first case is high priority). In a second scenario, the transmitter can specify that a second case is urgent and the receiver does not specify that the second case is urgent or high priority. In a third scenario, the transmitter does not specify that a third case is urgent, and the receiver does specify that the third case is urgent. In a fourth scenario, both the transmitter and receiver designate a fourth case as urgent.

With reference to the four scenarios mentioned above, there are a number of different ways in which the prioritization outcomes can be implemented. A first implementation can simply classify a case as urgent or not urgent, depending on whether either of the parties designated the case as urgent. For example, in the first scenario, neither the transmitter nor receiver designated the first case as urgent. As a result, for both the transmitter and the receiver, the first case would appear below the second, third, and fourth cases in the case listing. For other cases designated the same as the first case (no priority from either transmitter or receiver), the cases would be grouped together with the first case and would appear in chronological order. Under such an implementation, the second, third, and fourth cases would be designated urgent and treated the same because at least one party designated each of these cases as urgent. In this implementation, the second, third, and fourth cases can appear in chronological order in the case listing for each of the transmitter and recipient.

Another implementation could place each of the first, second, third, and fourth cases into a separate bucket. The fourth case and similar scenarios would appear in the case listing in chronological order and above the third case (and other cases prioritized the same as the third case), second case (and other cases prioritized the same as the second case), and first case (and other cases prioritized the same as the first case). With this implementation, the third case and similar scenarios would appear in chronological order and would be below the fourth case (and other cases prioritized the same as the fourth case) but above the first and second cases (and other cases prioritized the same as the first and second cases). Likewise, the second case and similar scenarios would appear in chronological order and would be below the fourth and third cases (and other cases prioritized the same as the fourth and third cases) and above the first case (and other cases prioritized the same as the first case). The first case and similar scenarios would be below the fourth, third, and second cases (and other cases prioritized the same as the fourth, third, and second cases).

In an alternative embodiment of this implementation, the positions of the second and third cases can be reversed, with the positioning of the fourth and first cases remaining the same. In such an embodiment, the second case and similar scenarios would appear in chronological order and would be below the fourth case (and other cases prioritized the same as the fourth case) but above the first and third cases (and other cases prioritized the same as the first and third cases). Also, the third case and similar scenarios appear in chronological order and would be below the fourth case and the second case (and other cases prioritized the same as the fourth case and the second case) but above the first case (and other cases prioritized the same as the first case).

In another implementation, the first through fourth cases can be placed into three different buckets. In this implementation, the fourth case and similar scenarios appear in chronological order ahead of the first, second, and third cases (and other cases prioritized the same as the first, second, and third cases). The second and third cases and similar scenarios are merged into a single bucket and presented in chronological order following the fourth case (and similar) and ahead of the first case (and similar). The first case and similar scenarios appear in chronological order below the fourth, third, and second cases (and similar).

Notwithstanding the embodiments described above in FIG. 1-14, various modifications and inclusions to those embodiments are contemplated and considered within the scope of the present disclosure. For example, while the figures have been described with specific reference to a medical application (e.g., the medical application 250), in other embodiments, the features described in this disclosure may be used for other types of applications that would benefit from having at least some of the features described herein. Furthermore and as noted above, the shape and form of the device 155, 160, 205, 210, 300, 405, 510, 605, 705, 900, and 1000 may change in other embodiments. Likewise, the shape, form, layout, text, fonts, font size, and other interactive features of the device 155, 160, 205, 210, 300, 405, 510, 605, 705, 900, and 1000, such as the various buttons, panels, etc. may vary in other embodiments. Furthermore, as used herein, the term "clicking" may include pressing (e.g., adding any amount of pressure on a physical button or on a virtual button portion of a display), single clicking, double clicking, tapping and holding, dragging, or any other maneuvers that may result in actuation of the area being "clicked."

Any of the operations described herein can be implemented as computer-readable instructions stored on a non-transitory computer-readable medium such as a computer memory.

It is also to be understood that the construction and arrangement of the elements of the systems and methods as shown in the representative embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed.

Accordingly, all such modifications are intended to be included within the scope of the present disclosure. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other illustrative embodiments without departing from scope of the present disclosure or from the scope of the appended claims.

Furthermore, functions and procedures described above may be performed by specialized equipment designed to perform the particular functions and procedures. The functions may also be performed by general-use equipment that executes commands related to the functions and procedures, or each function and procedure may be performed by a different piece of equipment with one piece of equipment serving as control or with a separate control device.

Moreover, although the figures show a specific order of method operations, the order of the operations may differ from what is depicted. Also, two or more operations may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection operations, processing operations, comparison operations, and decision operations.

What is claimed is:

1. A method, comprising:
receiving, by a receiver device, a request sent from a transmitter device, wherein the request is identified by a case name and at least one of a type of the request and a due date of the request, and wherein the request has a transmitter priority designated by the transmitter device;

assigning, by the receiver device, a receiver priority for the request received by the receiver device, wherein the receiver priority is based on an availability of the receiver device or a user of the receiver device;

determining a final priority by the receiver device, the final priority based upon a combination of the transmitter priority and the receiver priority;

setting, by the receiver device, one or more filters for the receiver priority, wherein the one or more filters prescribe an action to be taken with respect to the request based on a characteristic of the request regardless of the receiver priority; and handling the request within the receiver device based on the final priority and the one or more filters;

wherein the final priority is one of high or low, wherein if the final priority is low, notification of the request is postponed for as long as the receiver priority is active and wherein if the final priority is high, a notification of the request is not postponed.

2. The method of claim 1, wherein the transmitter priority is one of normal, urgent, and critical.

3. The method of claim 1, wherein the receiver priority is one of available, busy, limited availability, and do not disturb.

4. The method of claim 3, wherein the receiver priority is assigned by selecting one of the available, busy, limited availability, and do not disturb, and setting a reminder for a period of time such that the selected one of the receiver priority remains active until the reminder expires.

5. The method of claim 1, wherein the receiver priority is assigned for an indefinite period of time.

6. The method of claim 1, wherein the one or more filters allow the receiver device to receive the request from certain people regardless of the receiver priority.

7. The method of claim 1, wherein the receiver priority is do not disturb, the final priority is low.

8. The method of claim 1, wherein if the receiver priority is busy, the final priority is high if the transmitter priority of the request is critical and the final priority is low if the transmitter priority of the request is urgent or normal.

9. The method of claim 1, wherein if the receiver priority is limited availability, the final priority is high if the transmitter priority of the request is critical or urgent and the final priority is low if the transmitter priority of the request is normal.

10. The method of claim 1, wherein if the receiver priority is available, the final priority is high.

11. A receiver device comprising:
a memory configured to store application software;
a controller; and
a receiver configured to receive a request from a transmitter device, wherein the request is identified by a case name and at least one of a type of the request and a due date of the request, and wherein the request has a transmitter priority designated by the transmitter device; and wherein the controller is configured to:
assign the request a receiver priority, wherein the receiver priority is based on an availability of the receiver device or a user of the receiver device;
determine a final priority based upon the transmitter priority and the receiver priority;
set one or more filters for the receiver priority, wherein the one or more filters prescribe an action to be taken with respect to the request based on a characteristic of the request regardless of the receiver priority; and
manage notification of the request based upon the final priority and the one or more filters;

wherein the final priority is one of high or low, wherein if the final priority is low, notification of the request is postponed for as long as the receiver priority is active and wherein if the final priority is high, a notification of the request is not postponed.

12. The receiver device of claim 11, wherein the receiver device is a smart computing device.

13. The receiver device of claim 11, wherein the request is received through the application software.

14. A non-transitory computer-readable medium having instructions stored thereon that, upon execution by a computing device, cause the computing device to perform operations, the instructions comprising:

instructions to receive a request from a transmitter device, wherein the request is identified by a case name and at least one of a type of the request and a due date of the request, and wherein the request has a transmitter priority designated by the transmitter device;

instructions to assign a receiver priority to the request, wherein the receiver priority is based on an availability of a receiver device or a user of the receiver device;

instructions to determine a final priority based at least in part on the transmitter priority and the receiver priority;

instructions to set one or more filters for the receiver priority, wherein the one or more filters prescribe an action to be taken with respect to the request based on a characteristic of the request regardless of the receiver priority; and instructions to manage notification of the request based upon the final priority and the one or more filters;

wherein the final priority is one of high or low, wherein if the final priority is low, notification of the request is postponed for as long as the receiver priority is active and wherein if the final priority is high, a notification of the request is not postponed.

15. The non-transitory computer-readable medium of claim 14, wherein in addition to the transmitter priority, the request includes at least one of a case name, a type of request, a due date, text notes, audio notes, video notes, and photographic notes.

16. The non-transitory computer-readable medium of claim 14, wherein the request is used by at least one health care practitioner to communicate with at least one caregiver to facilitate care of at least one patient.

17. The non-transitory computer-readable medium of claim 14, wherein the instructions are accessible from a mobile platform or a web based platform.

18. The non-transitory computer-readable medium of claim 14, further comprising instructions to assign a date and time stamp to the request.

19. The non-transitory computer-readable medium of claim 14, further comprising instructions to at least one of add a new case, add participants to a case, add updates to a case, and keep track of time spent on a case.

* * * * *